US007135181B2

(12) United States Patent
Jensen et al.

(10) Patent No.: US 7,135,181 B2
(45) Date of Patent: Nov. 14, 2006

(54) METHOD FOR DOWN-REGULATION OF AMYLOID

(75) Inventors: Martin Roland Jensen, Holte (DK); Peter Birk Rasmussen, Frederiksberg (DK); Klaus Gregorius Nielsen, Soborg (DK)

(73) Assignee: Pharmexa A/S, Horsholm (DK)

( * ) Notice: Subject to any disclaimer, the term of this patent is extended or adjusted under 35 U.S.C. 154(b) by 592 days.

(21) Appl. No.: 09/785,215

(22) Filed: Feb. 20, 2001

(65) Prior Publication Data

US 2002/0187157 A1 Dec. 12, 2002

Related U.S. Application Data

(60) Provisional application No. 60/186,295, filed on Mar. 1, 2000.

(30) Foreign Application Priority Data

Feb. 21, 2000 (DK) .............................. 2000 00265

(51) Int. Cl.
*A61K 39/00* (2006.01)
*A61K 38/19* (2006.01)
*A61K 38/20* (2006.01)

(52) U.S. Cl. .................. 424/185.1; 424/85.1; 424/85.2

(58) Field of Classification Search ................ 530/300, 530/350; 514/2, 1; 424/185.1, 178.1, 184.1
See application file for complete search history.

(56) References Cited

U.S. PATENT DOCUMENTS 4,578,770 A 3/1986 Mitani
4,596,792 A 6/1986 Vyas
4,599,230 A 7/1986 Milich et al.
4,599,231 A 7/1986 Milich et al.
4,601,903 A 7/1986 Frasch
4,608,251 A 8/1986 Mia
5,192,688 A 3/1993 Switzer, III et al.
5,200,339 A 4/1993 Abraham
5,223,482 A 6/1993 Schilling, Jr.
5,851,996 A * 12/1998 Kline .......................... 514/12
5,874,469 A 2/1999 Maniar et al.
6,544,518 B1 * 4/2003 Friede et al. ............ 424/184.1
6,713,450 B1 * 3/2004 Frangione et al. ............ 514/12
6,787,144 B1 9/2004 Schenk et al.
6,787,523 B1 * 9/2004 Schenk ........................ 514/21
6,787,637 B1 * 9/2004 Schenk .................... 530/387.1
2002/0077288 A1 * 6/2002 Frangione et al. ............ 514/12
2002/0187157 A1 12/2002 Jensen et al.
2003/0068325 A1 * 4/2003 Wang ...................... 424/185.1
2003/0086938 A1 * 5/2003 Jensen et al. ............ 424/185.1
2003/0157117 A1 8/2003 Rasmussen et al.
2004/0062802 A1 4/2004 Hermelin
2004/0091945 A1 * 5/2004 Fitzer-Attas et al. ......... 435/7.2
2004/0141958 A1 7/2004 Steinaa et al.

FOREIGN PATENT DOCUMENTS

CL 1656-1995 7/1996
WO WO 93/15760 A1 8/1993
WO WO 93/23076 A1 11/1993
WO WO 95/07707 A1 3/1995
WO WO9505849 3/1995
WO WO9523166 8/1995
WO WO 96/13513 A1 5/1996
WO WO 98/23635 A1 4/1998
WO WO 99/24468 A1 5/1999
WO WO9927944 6/1999
WO WO 00/05316 A1 2/2000
WO WO 00/20027 A2 4/2000
WO WO 00/72880 A2 12/2000
WO WO 01/42306 A2 6/2001
WO WO 01/62282 A2 8/2001
WO WO 01/62284 A2 8/2001
WO WO 02/34777 * 5/2002
WO WO 01/39796 * 6/2002

OTHER PUBLICATIONS

Skolnick and Fetrow (2000) From Genes to Protein Strucuture and Function: Novel Applications of Compuational Approaches in the Genomic Era. Trends in Biotech 18(1); 34-39.*

Jobling et al, Mol. Microbiol., 1991, 5(7):1755-67.*

Jen et al. (1997) Preparation and Purification of antisera against different regions or isoforms of beta-amyloid precursor protein. Brain Research Protocols 2:23-30.*

Demattos et al. (2001) "Peripheral Anti Abeta Antibody Alters CNS and Plasma Abeta Clearance and Decreases Brain Abeta Bruden in a Mouse Model of Alzheimer's Disease" PNAS 10: 1-6.*

(Continued)

*Primary Examiner*—Janet L. Andres
*Assistant Examiner*—Gregory S. Emch
(74) *Attorney, Agent, or Firm*—Birch, Stewart, Kolasch & Birch, LLP

(57) ABSTRACT

A method for in vivo down-regulation of amyloid protein in an animal, including a human being, the method comprising effecting presentation to the animal's immune system of an immunogenically effective amount of at least one amyloidogenic polypeptide or subsequence thereof which has been formulated so that immunization of the animal with the amyloidgenic polypeptide or subsequence thereof induces production of antibodies against the amyloidogenic polypeptide, and/or at least one analogue of the amyloidogenic polypeptide wherein is introduced at least one modification in the amino acid sequence of the amyloidogenic polypeptide which has as a result the immunization of the animal with the analogue induces production of antibodies against the amyloidogenic polypeptide.

24 Claims, 1 Drawing Sheet

OTHER PUBLICATIONS

Perutz et al. (2002) "Amyloid Fibers are Water-Flled Nanotubes" PNAS 99(8): 5591-5595.*
Munch and Robinson (2002) Potential neurotoxic inflammatory responses to Abeta vaccination in humans. J Neural Transm 109: 1081-1087.*
Esiri (2001) Is an Effective Immune Intervention for Alzheimer's Disease in Prospect? Trends in Pharm Science 22(1): 2-3.*
Younkin (2001) Amyloid beta Vaccination: Reduced Plaques and Improved Cognition. Nature Medicine 7(1):18-19.*
Games et al. (1995) Alzheimer-type Neuropathology in Transgenic Mice overexpressing V717F beta-amyloid precursor protein. Nature 373(6514): 523-527.*
Raso (1998) Immunotherapy of Alzheimer's Disease Immunotherapy Weekly. Abstract.*
Schenk et al. (1999) Immunization with amyloid-beta attenuates Alzeimer-disease-like pathology in the PDAPP Mouse. Nature 400:173-177.*
Small et al. (2001) Alzheimer's Disease and Abeta Toxicity: from top to bottom. Nat Rev Neurosci. 2(8): 595-8.*
Chapman (2000) Model Behavior. Nature 408: 915-916.*
Lemere et al. (2000) Nasal Abeta Tratment Induces anti-Abeta antibody production and decreases cerebal amyloid burden in PD-APP mice. Annals of the NY Acad. Sci. 920: 328-331.*
Grubeck-Lobenstein et al. (2000) Immunization of beta-amyloid: could T-cell activation have a harmful effect? TINS 23: 114.*
Friedland et al. (1997) Neuroimaging of Vessel Amyloid in Alzheimer's Disease in Cerebrovascular Pathology in Alzheimer's Disease, eds. de la Torre and Hachinski, New York Academy of Science, NY, NY.*
Frenkel et al. (1998) N-terminal EFRH Sequence of Alzheimer's beta-amyloid peptide represents the epitope of its anti-aggregating antibodies. Journal of Neuroimmunology 88: 85-90.*
Frenkel et al. (2000) Immunization against Alzheimer's beta-amyloid plaques via EFRH phage adminstration. PNAS 97(21) 11455-11459.*
Frenkel et al. (1999) High Affinity Binding of Monoclonal Antibodies to the sequential epitope EFRH of beta-amyloid peptide is essential for modulation of fibrillar aggregation. Journal of Neuroimmunology 95: 136-142.*
ELAN "Elan and AHP Provide an Update on the Phase 2A Clinical Trial of AN-1792." Press Release (Jan. 28, 2002).*
ELAN "Elan and Wyeth Provide Update on Status of Alzheimer's Collaboration" Press Release (Mar. 1, 2002).*
Tanaka et al. (1998) NC-1900, an active Fragment analog of arginine vasopressin, improves learning and memory deficits induced by beta-amyloid protein in rats. European Journal of Pharmocology 352: 135-142.*
Tennet et al. (1995) Serum amyloid P component precents proteolysis of the amyloid fibrils of Alzheimer disease and systemic amyloidosis. PNAS 92: 4299-4303.*
Chen et al. (1998) Neurodegenerative Alzheimer-like pathology in PDAPP 717V—F transgenic mice. Progress in Brain Research 117: 327-334.*
Wells (1990) Additivity of Mutational Effects in Proteins. Biochemistry 29(37): 8509-8517.*
Bork (2000) Powers and Pitfalls in Sequence Analysis: The 70% Hurdle. Genome Research 10: 398-400.*
Doerks (1998) Protein Annotation: detective work for function prediction. TIG 14(6): 248-250.*
Smith and Zhang (1997) The Challenges of genome sequence annotation or "The Devil is in the details". Nature Biotechnology 15: 1222-1223.*
Brenner (1999) Erros in genome annotation. TIG 15(4): 132-133.*
Bork and Bairoch (1996) Go Hunting in sequence databases but watch out for the traps. TIG 12(10): 425-427.*
Ngo et al. (1995) The Protein Folding Problem and Tertiary Structure Prediction. 433-506.*
Sigurdsson et al. (2002) Immunization for Alzheimer's Disease. Drug Development Research 56: 135-142.*
Selkoe et al. (Feb. 20, 1987) "Conservation of Brain Amyloid Proteins in Aged Mammals and Humans with Alzheimer's Disease." Science 235(4791): 873-877.*
Johnstone et al. (Jul. 1991) "Conservation of the sequence of the Alzheimer's disease amyloid peptide in dog, polar bear and five other mammals by cross-species polymerase chain reaction analysis." Molecular Brain Research 10(4): 299-305.*
Eikelenboom et al. (2000) "Neuroinflammation and Alzheimer Disease: Clinical and Therapeutic Implications." Alzheimer Disease and Associated Disorders 14(Suppl. 1): S54-S61.*
Elan: News Jan. 28, 2002 "Elan and AHP provide an update on the phase 2A Clinical Trial of AN-1792."*
Bishop and Robinson (Nov./Dec. 2002) "The amyloid hypothesis: let sleeping dogmas lie?" Neurobiology of Aging 23(6): 1101-1105.*
Buttini, Manuel et al., "Expression of human apolipoprotein . . . ", The Journal of Neuroscience, Jun. 15, 1999, 19(12), pp. 4867-4880.
Clark, Lorraine N. et al., "Pathogenic implications of mutations . . . ", Proc. Natl. Acad. Sci. USA, Oct. 1998, vol. 95, pp. 13103-13107.
Hsiao, Karen, "Transgenic mice expresssing . . . ", Experimental Gerontology, vol. 33, 7-8,Nov./Dec. 1998 pp. 883-889.
Hutton, Mike et al., "Association of missense . . . ", Nature, vol. 393, Jun. 18, 1998, pp. 702-705.
Lippa, C.F. et al., "$A\beta_{-42}$ deposition precedes . . . ", The Lancet, Oct. 3, 1998, vol. 352, pp. 1117-1118.
Luo, Jin-Jun et al., "Death of PC12 cells . . . ", Journal of Neuroscience Research, (1999)55, pp. 629-642.
Naruse, Satoshi et al., "Effects of PS1 deficiency . . . ", Neuron, Nov. 1998, vol. 21, pp. 1213-1221.
Poorkjai, Parvoneh et al., "Tau is a candidate gene . . . ", Annals of Neurology, Jun. 1998, vol. 43, No. 6, pp. 815-825.
Schenk, Dale et al., "Immunization with amyloid-β . . . ", Nature, (Jul. 8, 1999) vol. 400, pp. 173-177.
Spillantini, Maria G. et al., "Mutation in the tau gene . . . ", Proc. Natl. Acad. Sci. USA, (1998)95pp. 7737-7741.
Strittmatter, Warren J. et al., "Apolipoprotein E: high-avidity . . . ", Proc. Natl. Sci. USA, Mar. 1993, vol. 90, pp. 1977-1981.
Vidal, Ruben et al., "A stop-codon mutation . . . ", Nature, (Jun. 24, 1999)vol. 399, pp. 776-781.
Zhehng, H. et al., "Mice deficient for the amyloid . . . ", Annals New York Accademy of Sciences, Ann N Y Acad Sci., (Jan. 17, 1996)777, pp. 421-426.
McLaurin, J. et al., Therapeutically effective antibodies against amyloid-B peptide target amyloid-B residues 4-10 and inhibit cytotoxicity and fibrillogenesis; Nature Medicine, published online Oct. 15, 2002.
Monsonego, A. et al., Immune hyporesponsiveness to amyloid B-peptide in amyloid precursor protein transgenic mice: Implications for the pathogenesis and treatment of Alzheimer's disease; PNAS, Aug. 28, 2001, vol. 98, No. 18, pp. 10273-10278.
Nature Medicine (NEWS), vol. 8, No. 3, Mar. 2002, pp. 199-200, 2002 Nature Publishing Group.
Nerve inflammation halts trial for Alzheimer's drug; Nature (news), vol. 415, Jan. 31, 2002.
Nicoll et al., Neuropathology of human Alzheimer disease after immunization with amyloid-B peptide; a case report; Nature Medicine, published online Mar. 17, 2003.
Holcomb et al., Accelerated Alzheimer-type phenotype in transgenic mice carrying both mutant amyloid precursor protein and preseniline 1 transgene; Nature Medicine, vol. 4, No. 1, Jan. 1998, pp. 97-100.
Schenk et al., Immunization with amyloid-B attenuates Alzheimer-disease-like pathology in the PDAPP mouse, Nature, vol. 400, Jul. 8, 1999, pp. 173-177.
Gupta et al., Hyperexpression of biologically active human chorionic gonadotropin using the methyltropic yeast, *Pichia pastoris*, Journal of Molecular Endocrinology (1999) 22, 273-283.
Janus et al., A beta peptide immunization reduces behavioural impairment and plaques in a model of Alzheimer's disease, Nature, vol. 408, Dec. 21/28, 2000, pp. 979-982.

Kas, H. S., Chitosan: properties, preparation and application to microparticulate systems, Journal of Microencapsulation, 1997, vol. 14, No. 6, 689-711.
Lees, A. et al., Enhanced immunogenicity of protein-dextran conjugates: I. Rapid stiulation of enhanded antibody responses to poorly immunogenic molecules, Vaccine 1994, vol. 12, No. 13, pp. 1160-1166.
Leon, J. et al., Alzheimer's Disease Care: Costs and Potential Savings, Health Affairs, vol. 17, No. 6, 1998, pp. 206-216.
Shekunov, B. Yu et al., Crystallization process in turbulent supercritical flows, Journal of Crystal Growth 198/199 (1999), pp. 1345-1351.
(Abstract) Chilean Patent Application No. 01656-1995, published Aug. 8, 1996.
Calvo-Calle et al. (Feb. 15, 1993), "Immunogenicity of Multiple Antigent Peptides Containing B and Non-Repeat T cell Epitopes of the Circumsporozoite Protein of *Plasmodium falciparu*" The Journal of Immunology 150(4): 1403-1412.
Goldsby et al. (2002) Kuby Immunology, Chapter 1, "Overview of the Immune System", (pp. 3-25).
Goldsby et al. (2002) Kuby Immunology, Chapter 18, "Vaccines", (pp. 449-465).
Marguerite, M. et al. (Jun. 1992), "Analysis of Antigenicity and Immunogenicity of five Different Chemically Defined Constructs of a Peptide", Molecular Immunology, vol. 29(6): 793-800.
Otvos, Jr. et al. (Jan. 13, 2000), "In situ stimulation of a T helper cell hybridoma with a cellulose-bound peptide antigen", Journal of Immunological methods 233(1-2):95-105.
Sela et al. ( Apr. 1992), "A Tale of Two Peptides, TyrTyrGluGlu and TryGluTryGlu, and their Diverse Immune Behavior", Behring Inst. Mitt. 91:54-66.
Dictionary.com retrieved from Internet on Dec. 16, 2004 (including but not limited to American Heritage Dictionary of the English Language 2002).
Panina-Bordignon et al. (Dec. 1989) "University immunogenic T cell epitopes: promiscuous binding to human MHC class II and promiscuous recognition by T cells." Eur J. Immunol. 19(12): 2237-42.

* cited by examiner

SEQUENCE LISTING

```
<160> NUMBER OF SEQ ID NOS: 19

<210> SEQ ID NO 1
<211> LENGTH: 2313
<212> TYPE: DNA
<213> ORGANISM: Homo sapiens
<220> FEATURE:
<221> NAME/KEY: CDS
<222> LOCATION: (1)..(2313)
<223> OTHER INFORMATION:
<221> NAME/KEY: misc_feature
<222> LOCATION: (2098)..(2169)
<223> OTHER INFORMATION: nucleotides encoding transmembrane region
<221> NAME/KEY: misc_feature
<222> LOCATION: (2014)..(2313)
<223> OTHER INFORMATION: Nucleotides encoding C-100
<221> NAME/KEY: misc_feature
<222> LOCATION: (2016)..(2144)
<223> OTHER INFORMATION: Abeta 42/43
<221> NAME/KEY: misc_feature
<222> LOCATION: (2014)..(2142)
<223> OTHER INFORMATION: Abeta 42/43

<400> SEQUENCE: 1

atg ctg ccc ggt ttg gca ctg ctc ctg ctg gcc gcc tgg acg gct cgg       48
Met Leu Pro Gly Leu Ala Leu Leu Leu Leu Ala Ala Trp Thr Ala Arg
1               5                   10                  15

gcg ctg gag gta ccc act gat ggt aat gct ggc ctg ctg gct gaa ccc       96
Ala Leu Glu Val Pro Thr Asp Gly Asn Ala Gly Leu Leu Ala Glu Pro
            20                  25                  30

cag att gcc atg ttc tgt ggc aga ctg aac atg cac atg aat gtc cag      144
Gln Ile Ala Met Phe Cys Gly Arg Leu Asn Met His Met Asn Val Gln
        35                  40                  45

aat ggg aag tgg gat tca gat cca tca ggg acc aaa acc tgc att gat      192
Asn Gly Lys Trp Asp Ser Asp Pro Ser Gly Thr Lys Thr Cys Ile Asp
    50                  55                  60

acc aag gaa ggc atc ctg cag tat tgc caa gaa gtc tac cct gaa ctg      240
Thr Lys Glu Gly Ile Leu Gln Tyr Cys Gln Glu Val Tyr Pro Glu Leu
65                  70                  75                  80

cag atc acc aat gtg gta gaa gcc aac caa cca gtg acc atc cag aac      288
Gln Ile Thr Asn Val Val Glu Ala Asn Gln Pro Val Thr Ile Gln Asn
                85                  90                  95

tgg tgc aag cgg ggc cgc aag cag tgc aag acc cat ccc cac ttt gtg      336
Trp Cys Lys Arg Gly Arg Lys Gln Cys Lys Thr His Pro His Phe Val
            100                 105                 110

att ccc tac cgc tgc tta gtt ggt gag ttt gta agt gat gcc ctt ctc      384
Ile Pro Tyr Arg Cys Leu Val Gly Glu Phe Val Ser Asp Ala Leu Leu
        115                 120                 125

gtt cct gac aag tgc aaa ttc tta cac cag gag agg atg gat gtt tgc      432
Val Pro Asp Lys Cys Lys Phe Leu His Gln Glu Arg Met Asp Val Cys
    130                 135                 140

gaa act cat ctt cac tgg cac acc gtc gcc aaa gag aca tgc agt gag      480
Glu Thr His Leu His Trp His Thr Val Ala Lys Glu Thr Cys Ser Glu
145                 150                 155                 160

aag agt acc aac ttg cat gac tac ggc atg ttg ctg ccc tgc gga att      528
Lys Ser Thr Asn Leu His Asp Tyr Gly Met Leu Leu Pro Cys Gly Ile
                165                 170                 175

gac aag ttc cga ggg gta gag ttt gtg tgt tgc cca ctg gct gaa gaa      576
Asp Lys Phe Arg Gly Val Glu Phe Val Cys Cys Pro Leu Ala Glu Glu
            180                 185                 190

agt gac aat gtg gat tct gct gat gcg gag gag gat gac tcg gat gtc      624
Ser Asp Asn Val Asp Ser Ala Asp Ala Glu Glu Asp Asp Ser Asp Val
        195                 200                 205
```

-continued

```
tgg tgg ggc gga gca gac aca gac tat gca gat ggg agt gaa gac aaa      672
Trp Trp Gly Gly Ala Asp Thr Asp Tyr Ala Asp Gly Ser Glu Asp Lys
    210                 215                 220

gta gta gaa gta gca gag gag gaa gaa gtg gct gag gtg gaa gaa gaa      720
Val Val Glu Val Ala Glu Glu Glu Glu Val Ala Glu Val Glu Glu Glu
225                 230                 235                 240

gaa gcc gat gat gac gag gac gat gag gat ggt gat gag gta gag gaa      768
Glu Ala Asp Asp Asp Glu Asp Asp Glu Asp Gly Asp Glu Val Glu Glu
                245                 250                 255

gag gct gag gaa ccc tac gaa gaa gcc aca gag aga acc acc agc att      816
Glu Ala Glu Glu Pro Tyr Glu Glu Ala Thr Glu Arg Thr Thr Ser Ile
            260                 265                 270

gcc acc acc acc acc acc acc aca gag tct gtg gaa gag gtg gtt cga      864
Ala Thr Thr Thr Thr Thr Thr Thr Glu Ser Val Glu Glu Val Val Arg
        275                 280                 285

gag gtg tgc tct gaa caa gcc gag acg ggg ccg tgc cga gca atg atc      912
Glu Val Cys Ser Glu Gln Ala Glu Thr Gly Pro Cys Arg Ala Met Ile
    290                 295                 300

tcc cgc tgg tac ttt gat gtg act gaa ggg aag tgt gcc cca ttc ttt      960
Ser Arg Trp Tyr Phe Asp Val Thr Glu Gly Lys Cys Ala Pro Phe Phe
305                 310                 315                 320

tac ggc gga tgt ggc ggc aac cgg aac aac ttt gac aca gaa gag tac     1008
Tyr Gly Gly Cys Gly Gly Asn Arg Asn Asn Phe Asp Thr Glu Glu Tyr
                325                 330                 335

tgc atg gcc gtg tgt ggc agc gcc atg tcc caa agt tta ctc aag act     1056
Cys Met Ala Val Cys Gly Ser Ala Met Ser Gln Ser Leu Leu Lys Thr
            340                 345                 350

acc cag gaa cct ctt gcc cga gat cct gtt aaa ctt cct aca aca gca     1104
Thr Gln Glu Pro Leu Ala Arg Asp Pro Val Lys Leu Pro Thr Thr Ala
        355                 360                 365

gcc agt acc cct gat gcc gtt gac aag tat ctc gag aca cct ggg gat     1152
Ala Ser Thr Pro Asp Ala Val Asp Lys Tyr Leu Glu Thr Pro Gly Asp
    370                 375                 380

gag aat gaa cat gcc cat ttc cag aaa gcc aaa gag agg ctt gag gcc     1200
Glu Asn Glu His Ala His Phe Gln Lys Ala Lys Glu Arg Leu Glu Ala
385                 390                 395                 400

aag cac cga gag aga atg tcc cag gtc atg aga gaa tgg gaa gag gca     1248
Lys His Arg Glu Arg Met Ser Gln Val Met Arg Glu Trp Glu Glu Ala
                405                 410                 415

gaa cgt caa gca aag aac ttg cct aaa gct gat aag aag gca gtt atc     1296
Glu Arg Gln Ala Lys Asn Leu Pro Lys Ala Asp Lys Lys Ala Val Ile
            420                 425                 430

cag cat ttc cag gag aaa gtg gaa tct ttg gaa cag gaa gca gcc aac     1344
Gln His Phe Gln Glu Lys Val Glu Ser Leu Glu Gln Glu Ala Ala Asn
        435                 440                 445

gag aga cag cag ctg gtg gag aca cac atg gcc aga gtg gaa gcc atg     1392
Glu Arg Gln Gln Leu Val Glu Thr His Met Ala Arg Val Glu Ala Met
    450                 455                 460

ctc aat gac cgc cgc cgc ctg gcc ctg gag aac tac atc acc gct ctg     1440
Leu Asn Asp Arg Arg Arg Leu Ala Leu Glu Asn Tyr Ile Thr Ala Leu
465                 470                 475                 480

cag gct gtt cct cct cgg cct cgt cac gtg ttc aat atg cta aag aag     1488
Gln Ala Val Pro Pro Arg Pro Arg His Val Phe Asn Met Leu Lys Lys
                485                 490                 495

tat gtc cgc gca gaa cag aag gac aga cag cac acc cta aag cat ttc     1536
Tyr Val Arg Ala Glu Gln Lys Asp Arg Gln His Thr Leu Lys His Phe
            500                 505                 510

gag cat gtg cgc atg gtg gat ccc aag aaa gcc gct cag atc cgg tcc     1584
Glu His Val Arg Met Val Asp Pro Lys Lys Ala Ala Gln Ile Arg Ser
```

-continued 515 520 525 cag gtt atg aca cac ctc cgt gtg att tat gag cgc atg aat cag tct 1632
Gln Val Met Thr His Leu Arg Val Ile Tyr Glu Arg Met Asn Gln Ser
530 535 540 ctc tcc ctg ctc tac aac gtg cct gca gtg gcc gag gag att cag gat 1680
Leu Ser Leu Leu Tyr Asn Val Pro Ala Val Ala Glu Glu Ile Gln Asp
545 550 555 560 gaa gtt gat gag ctg ctt cag aaa gag caa aac tat tca gat gac gtc 1728
Glu Val Asp Glu Leu Leu Gln Lys Glu Gln Asn Tyr Ser Asp Asp Val
565 570 575 ttg gcc aac atg att agt gaa cca agg atc agt tac gga aac gat gct 1776
Leu Ala Asn Met Ile Ser Glu Pro Arg Ile Ser Tyr Gly Asn Asp Ala
580 585 590 ctc atg cca tct ttg acc gaa acg aaa acc acc gtg gag ctc ctt ccc 1824
Leu Met Pro Ser Leu Thr Glu Thr Lys Thr Thr Val Glu Leu Leu Pro
595 600 605 gtg aat gga gag ttc agc ctg gac gat ctc cag ccg tgg cat tct ttt 1872
Val Asn Gly Glu Phe Ser Leu Asp Asp Leu Gln Pro Trp His Ser Phe
610 615 620 ggg gct gac tct gtg cca gcc aac aca gaa aac gaa gtt gag cct gtt 1920
Gly Ala Asp Ser Val Pro Ala Asn Thr Glu Asn Glu Val Glu Pro Val
625 630 635 640 gat gcc cgc cct gct gcc gac cga gga ctg acc act cga cca ggt tct 1968
Asp Ala Arg Pro Ala Ala Asp Arg Gly Leu Thr Thr Arg Pro Gly Ser
645 650 655 ggg ttg aca aat atc aag acg gag gag atc tct gaa gtg aag atg gat 2016
Gly Leu Thr Asn Ile Lys Thr Glu Glu Ile Ser Glu Val Lys Met Asp
660 665 670 gca gaa ttc cga cat gac tca gga tat gaa gtt cat cat caa aaa ttg 2064
Ala Glu Phe Arg His Asp Ser Gly Tyr Glu Val His His Gln Lys Leu
675 680 685 gtg ttc ttt gca gaa gat gtg ggt tca aac aaa ggt gca atc att gga 2112
Val Phe Phe Ala Glu Asp Val Gly Ser Asn Lys Gly Ala Ile Ile Gly
690 695 700 ctc atg gtg ggc ggt gtt gtc ata gcg aca gtg atc gtc atc acc ttg 2160
Leu Met Val Gly Gly Val Val Ile Ala Thr Val Ile Val Ile Thr Leu
705 710 715 720 gtg atg ctg aag aag aaa cag tac aca tcc att cat cat ggt gtg gtg 2208
Val Met Leu Lys Lys Lys Gln Tyr Thr Ser Ile His His Gly Val Val
725 730 735 gag gtt gac gcc gct gtc acc cca gag gag cgc cac ctg tcc aag atg 2256
Glu Val Asp Ala Ala Val Thr Pro Glu Glu Arg His Leu Ser Lys Met
740 745 750 cag cag aac ggc tac gaa aat cca acc tac aag ttc ttt gag cag atg 2304
Gln Gln Asn Gly Tyr Glu Asn Pro Thr Tyr Lys Phe Phe Glu Gln Met
755 760 765 cag aac tag 2313
Gln Asn
770

<210> SEQ ID NO 2
<211> LENGTH: 770
<212> TYPE: PRT
<213> ORGANISM: Homo sapiens

<400> SEQUENCE: 2

Met Leu Pro Gly Leu Ala Leu Leu Leu Leu Ala Ala Trp Thr Ala Arg
1 5 10 15

Ala Leu Glu Val Pro Thr Asp Gly Asn Ala Gly Leu Leu Ala Glu Pro
20 25 30

-continued

```
Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445
```

-continued

```
Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 3
<211> LENGTH: 45
<212> TYPE: DNA
<213> ORGANISM: Clostridium tetani
<220> FEATURE:
<221> NAME/KEY: CDS
<222> LOCATION: (1)..(45)
<223> OTHER INFORMATION: DNA encoding P2 epitope

<400> SEQUENCE: 3

cag tac atc aaa gct aac tcc aaa ttc atc ggt atc acc gag ctg          45
Gln Tyr Ile Lys Ala Asn Ser Lys Phe Ile Gly Ile Thr Glu Leu
1               5                   10                  15
```

-continued

<210> SEQ ID NO 4
<211> LENGTH: 15
<212> TYPE: PRT
<213> ORGANISM: Clostridium tetani

<400> SEQUENCE: 4

```
Gln Tyr Ile Lys Ala Asn Ser Lys Phe Ile Gly Ile Thr Glu Leu
1               5                   10                  15
```

<210> SEQ ID NO 5
<211> LENGTH: 63
<212> TYPE: DNA
<213> ORGANISM: Clostridium tetani
<220> FEATURE:
<221> NAME/KEY: CDS
<222> LOCATION: (1)..(63)
<223> OTHER INFORMATION: DNA encoding P30 epitope

<400> SEQUENCE: 5

```
ttc aac aac ttc acc gta agc ttc tgg ctg cgt gtt ccg aaa gtt agc       48
Phe Asn Asn Phe Thr Val Ser Phe Trp Leu Arg Val Pro Lys Val Ser
1               5                   10                  15

gct agc cac ctg gaa                                                   63
Ala Ser His Leu Glu
            20
```

<210> SEQ ID NO 6
<211> LENGTH: 21
<212> TYPE: PRT
<213> ORGANISM: Clostridium tetani

<400> SEQUENCE: 6

```
Phe Asn Asn Phe Thr Val Ser Phe Trp Leu Arg Val Pro Lys Val Ser
1               5                   10                  15

Ala Ser His Leu Glu
            20
```

<210> SEQ ID NO 7
<211> LENGTH: 21
<212> TYPE: DNA
<213> ORGANISM: Artificial Sequence
<220> FEATURE:
<223> OTHER INFORMATION: Primer targeted to the pAB1 plasmid

<400> SEQUENCE: 7

```
caactcagct tcctttcggg c                                               21
```

<210> SEQ ID NO 8
<211> LENGTH: 21
<212> TYPE: DNA
<213> ORGANISM: Artificial Sequence
<220> FEATURE:
<223> OTHER INFORMATION: Primer targeted to the pAB1 plasmid

<400> SEQUENCE: 8

```
agatctcgat cccgcgaaat t                                               21
```

<210> SEQ ID NO 9
<211> LENGTH: 135
<212> TYPE: DNA
<213> ORGANISM: Artificial Sequence
<220> FEATURE:
<223> OTHER INFORMATION: Primer that encodes the human abeta-43 fragment
with E. coli optimised codons

<400> SEQUENCE: 9

-continued

```
atggatgcag aattccgtca cgactccggt tacgaagttc accaccagaa actggttttc     60

ttcgcagaag atgttggttc caacaaaggt gcaatcatcg gtctgatggt tggcggtgtt    120

gttatcgcga cctag                                                     135


<210> SEQ ID NO 10
<211> LENGTH: 31
<212> TYPE: DNA
<213> ORGANISM: Artificial Sequence
<220> FEATURE:
<223> OTHER INFORMATION: Primer derived from SEQ ID NO:9

<400> SEQUENCE: 10

gccggccatg gatgcagaat tccgtcacga c                                    31


<210> SEQ ID NO 11
<211> LENGTH: 39
<212> TYPE: DNA
<213> ORGANISM: Artificial Sequence
<220> FEATURE:
<223> OTHER INFORMATION: Primer derived from SEQ ID NO:9

<400> SEQUENCE: 11

gccggaagct tctaggtcgc gataacaaca ccgccaacc                            39


<210> SEQ ID NO 12
<211> LENGTH: 84
<212> TYPE: DNA
<213> ORGANISM: Artificial Sequence
<220> FEATURE:
<223> OTHER INFORMATION: Primer encoding the P2 epitope

<400> SEQUENCE: 12

ccggcaagct tctacagctc ggtgataccg atgaatttgg agttagcttt gatgtactgg     60

gtcgcgataa caacaccgcc aacc                                            84


<210> SEQ ID NO 13
<211> LENGTH: 101
<212> TYPE: DNA
<213> ORGANISM: Artificial Sequence
<220> FEATURE:
<223> OTHER INFORMATION: Primer derived from the pAB1 plasmid

<400> SEQUENCE: 13

gccggccatg ggtttcaaca acttcaccgt tagcttctgg ctgcgtgttc cgaaagttag     60

cgcgagccac ctggaagatg cagaattccg tcacgactcc g                        101


<210> SEQ ID NO 14
<211> LENGTH: 172
<212> TYPE: DNA
<213> ORGANISM: Artificial Sequence
<220> FEATURE:
<223> OTHER INFORMATION: Primer derived from the pAB2 plasmid

<400> SEQUENCE: 14

gggccaagct tggatccggt cgcgataaca acaccgccaa ccatcagacc gatgattgca     60

cctttgttgg aaccaacatc ttctgcgaag aaaaccagtt tctggtggtg aacttcgtaa    120

ccggagtcgt gacggaactc tgcatccagc tcggtgatac cgatgaattt gg            172


<210> SEQ ID NO 15
<211> LENGTH: 30
<212> TYPE: DNA
```

-continued

<213> ORGANISM: Artificial Sequence
<220> FEATURE:
<223> OTHER INFORMATION: Primer derived from the pAB3 plasmid

<400> SEQUENCE: 15
ctggaagatg cagagttccg tcacgactcc 30

<210> SEQ ID NO 16
<211> LENGTH: 35
<212> TYPE: DNA
<213> ORGANISM: Artificial Sequence
<220> FEATURE:
<223> OTHER INFORMATION: Primer derived from the pAB3 plasmid

<400> SEQUENCE: 16
gcgccggatc cttcaacaac ttcaccgtta gcttc 35

<210> SEQ ID NO 17
<211> LENGTH: 8
<212> TYPE: DNA
<213> ORGANISM: Artificial Sequence
<220> FEATURE:
<223> OTHER INFORMATION: Artificial sequence, used as an example for how to calculate sequence identity, has 75% sequence identity with SEQ ID NO:18

<400> SEQUENCE: 17 agtcagtc 8

<210> SEQ ID NO 18
<211> LENGTH: 8
<212> TYPE: DNA
<213> ORGANISM: Artificial Sequence
<220> FEATURE:
<223> OTHER INFORMATION: Artificial sequence, used as an example for how to calculate sequence identity, has 75% sequence identity with SEQ ID NO:17

<400> SEQUENCE: 18 aatcaatc 8

<210> SEQ ID NO 19
<211> LENGTH: 13
<212> TYPE: PRT
<213> ORGANISM: Artificial Sequence
<220> FEATURE:
<223> OTHER INFORMATION: artificial T-cell epitope capable of binding to a large portion of MHC Class II molecules in a variety of animals

<400> SEQUENCE: 19

```
Ala Lys Phe Val Ala Ala Trp Thr Leu Lys Ala Ala Ala
1               5                   10
```

METHOD FOR DOWN-REGULATION OF AMYLOID

This application claims priority to provisional U.S. Application No. 60/186,295 filed on Mar. 1, 2000, the entire contents of which are incorporated by reference, under 35 U.S.C. §119(e). This application also claims priority to Danish application PA 2000 00265 filed on Feb. 21, 2000 under 35 U.S.C. §119(d).

FIELD OF THE INVENTION

The present invention relates to improvements in therapy and prevention of Alzheimer's disease (AD) and other diseases characterized by deposition of amyloid, e.g. characterized by amyloid deposits in the central nervous system (CNS). More specifically, the present invention provides a method for down-regulating (undesired) deposits of amyloid by enabling the production of antibodies against the relevant protein or components thereof in subjects suffering from or in danger of suffering from diseases having a pathology involving amyloid deposition. The invention also provides for methods of producing polypeptides useful in this method as well as for the modified polypeptides as such. Also encompassed by the present invention are nucleic acid fragments encoding the modified polypeptides as well as vectors incorporating these nucleic acid fragments and host cells and cell lines transformed therewith. The invention also provides for a method for the identification of analogues of the deposit polypeptides which are useful in the method of the invention as well as for compositions comprising modified polypeptides or comprising nucleic acids encoding modified polypeptides.

BACKGROUND OF THE INVENTION

Amyloidosis is the extracellular deposition of insoluble protein fibrils leading to tissue damage and disease (Pepys, 1996; Tan et al., 1995; Kelly, 1996). The fibrils form when normally soluble proteins and peptides self-associate in an abnormal manner (Kelly, 1997). Amyloid is associated with serious diseases including systemic amyloidosis, AD, maturity onset diabetes, Parkinson's disease, Huntington's disease, fronto-temporal dementia and the prion-related transmissible spongiform encephalopathies (kuru and Creutzfeldt-Jacob disease in humans and scrapie and BSE in sheep and cattle, respectively) and the amyloid plaque formation in for instance Alzheimer's seems to be closely associated with the progression of human disease. In animal models over-expression, or the expression of modified forms, of proteins found in deposits, like the β-amyloid protein, has been shown to induce various symptoms of disease, e.g. Alzheimer's-like symptoms. There is no specific treatment for amyloid deposition and these diseases are usually fatal.

The subunits of amyloid fibrils may be wild-type, variant or truncated proteins, and similar fibrils can be formed in vitro from oligopeptides and denatured proteins (Bradbury et al., 1960; Filshie et al., 1964; Burke & Rougvie, 1972). The nature of the polypeptide component of the fibrils defines the character of the amyloidosis. Despite large differences in the size, native structure and function of amyloid proteins, all amyloid fibrils are of indeterminate length, unbranched, 70 to 120 Å in diameter, and display characteristic staining with Congo Red (Pepys, 1996). They are characteristic of a cross-β structure (Pauling & Corey, 1951) in which the polypeptide chain is organized in β-sheets. Although the amyloid proteins have very different precursor structures, they can all undergo a structural conversion, perhaps along a similar pathway, to a misfolded form that is the building block of the β-sheet helix protofilament.

This distinctive fibre pattern led to the amyloidoses being called the β-fibrilloses (Glenner, 1980a,b), and the fibril protein of AD was named the β-protein before its secondary structure was known (Glenner & Wong, 1984). The characteristic cross-β diffraction pattern, together with the fibril appearance and tinctorial properties are now the accepted diagnostic hallmarks of amyloid, and suggest that the fibrils, although formed from quite different protein precursors, share a degree of structural similarity and comprise a structural superfamily, irrespective of the nature of their precursor proteins (Sunde M, Serpell L C, Bartlam M, Fraser P E, Pepys M B, Blake CCFJ Mol Biol 1997 Oct. 31; 273(3):729–739).

One of the most widespread and well-known diseases where amyloid deposits in the central nervus system are suggested to have a central role in the progression of the disease, is AD.

AD

Alzheimer's disease (AD) is an irreversible, progressive brain disorder that occurs gradually and results in memory loss, behavioural and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last for up to 20 years.

AD advances by stages, from early, mild forgetfulness to a severe loss of mental function. This loss is known as dementia. In most people with AD, symptoms first appear after the age of 60, but earlier onsets are not infrequent. The earliest symptoms often include loss of recent memory, faulty judgment, and changes in personality. Often, people in the initial stages of AD think less clearly and forget the names of familiar people and common objects. Later in the disease, they may forget how to do even simple tasks. Eventually, people with AD lose all reasoning ability and become dependent on other people for their everyday care. Ultimately, the disease becomes so debilitating that patients are bedridden and likely to develop other illnesses and infections. Most commonly, people with AD die from pneumonia.

Although the risk of developing AD increases with age, AD and dementia symptoms are not a part of normal aging. AD and other dementing disorders are caused by diseases that affect the brain. In normal aging, nerve cells in the brain are not lost in large numbers. In contrast, AD disrupts three key processes: Nerve cell communication, metabolism, and repair. This disruption ultimately causes many nerve cells to stop functioning, lose connections with other nerve cells, and die.

At first, AD destroys neurons in parts of the brain that control memory, especially in the hippocampus and related structures. As nerve cells in the hippocampus stop functioning properly, short-term memory fails, and often, a person's ability to do easy and familiar tasks begins to decline. AD also attacks the cerebral cortex, particularly the areas responsible for language and reasoning. Eventually, many other areas of the brain are involved, all these brain regions atrophy (shrink), and the AD patient becomes bedridden, incontinent, totally helpless, and unresponsive to the outside world (source: National Institute on Aging Progress Report on Alzheimer's Disease, 1999).

The Impact of AD

AD is the most common cause of dementia among people age 65 and older. It presents a major health problem because of its enormous impact on individuals, families, the health care system, and society as a whole. Scientists estimate that up to 4 million people currently suffer from the disease, and the prevalence doubles every 5 years beyond age 65. It is also estimated that approximately 360,000 new cases (incidence) will occur each year, though this number will increase as the population ages (Brookmeyer et al., 1998).

AD puts a heavy economic burden on society. A recent study in the United States estimated that the annual cost of caring for one AD patient is $18,408 for a patient with mild AD, $30,096 for a patient with moderate AD, and $36,132 for a patient with severe AD. The annual national cost of caring for AD patients in the US is estimated to be slightly over $50 billion (Leon et al., 1998).

Approximately 4 million Americans are 85 or older, and in most industrialized countries, this age group is one of the fastest growing segments of the population. It is estimated that this group will number nearly 8.5 million by the year 2030 in the US; some experts who study population trends suggest that the number could be even greater. As more and more people live longer, the number of people affected by diseases of aging, including AD, will continue to grow. For example, some studies show that nearly half of all people age 85 and older have some form of dementia. (National Institute on Aging Progress Report on Alzheimer's Disease, 1999)

The Main Characteristics of AD

Two abnormal structures in the brain are the hallmarks of AD: amyloid plaques and neurofibrillary tangles (NFT). Plaques are dense, largely insoluble deposits of protein and cellular material outside and around the brain's neurons. Tangles are insoluble twisted fibres that build up inside neurons.

Two types of AD exist: familial AD (FAD), which follows a certain pattern of inheritance, and sporadic AD, where no obvious pattern of inheritance is seen. Because of differences in the age at onset, AD is further described as early-onset (occurring in people younger than 65) or late-onset (occurring in those 65 and older). Early-onset AD is rare (about 10 percent of cases) and generally affects people aged 30 to 60. Some forms of early-onset AD are inherited and run in families. Early-onset AD also often progresses faster than the more common, late-onset form.

All FADs known so far have an early onset, and as many as 50 percent of FAD cases are now known to be caused by defects in three genes located on three different chromosomes. These are mutations in the APP gene on chromosome 21; mutations in a gene on chromosome 14, called presenilin 1; and mutations in a gene on chromosome 1, called presenilin 2. There is as yet no evidence, however, that any of these mutations play a major role in the more common, sporadic or non-familial form of late-onset AD. (National Institute on Aging Progress Report on Alzheimer's Disease, 1999)

Amyloid Plaques

In AD, amyloid plaques develop first in areas of the brain used for memory and other cognitive functions. They consist of largely insoluble deposits of beta amyloid (hereinafter designated Aβ)—a protein fragment of a larger protein called amyloid precursor protein (APP, the amino acid sequence of which is set forth in SEQ ID NO: 2)—intermingled with portions of neurons and with non-nerve cells such as microglia and astrocytes. It is not known whether amyloid plaques themselves constitute the main cause of AD or whether they are a by-product of the AD process. Certainly, changes in the APP protein can cause AD, as shown in the inherited form of AD caused by mutations in the APP gene, and Aβ plaque formation seems to be closely associated with the progression of the human disease (Lippa C. F. et al. 1998).

APP

APP is one of many proteins that are associated with cell membranes. After it is made, APP becomes embedded in the nerve cell's membrane, partly inside and partly outside the cell. Recent studies using transgenic mice demonstrate that APP appears to play an important role in the growth and survival of neurons. For example, certain forms and amounts of APP may protect neurons against both short- and long-term damage and may render damaged neurons better able to repair themselves and help parts of neurons grow after brain injury.

While APP is embedded in the cell membrane, proteases act on particular sites in APP, cleaving it into protein fragments. One protease helps cleave APP to form Aβ, and another protease cleaves APP in the middle of the amyloid fragment so that Aβ cannot be formed. The Aβ formed is of two different lengths, a shorter 40 (or 41) amino acids Aβ that is relatively soluble and aggregates slowly, and a slightly longer, 42 amino acids "sticky" Aβ that rapidly forms insoluble clumps. While Aβ is being formed, it is not yet known exactly how it moves through or around nerve cells. In the final stages of this process, the "sticky" Aβ aggregates into long filaments outside the cell and, along with fragments of dead and dying neurons and the microglia and astrocytes, forms the plaques that are characteristic of AD in brain tissue.

Some evidence exists that the mutations in APP render more likely that Aβ will be snipped out of the APP precursor, thus causing either more total Aβ or relatively more of the "sticky" form to be made. It also appears that mutations in the presenilin genes may contribute to the degeneration of neurons in at least two ways: By modifying Aβ production or by triggering the death of cells more directly. Other researchers suggest that mutated presenilins 1 and 2 may be involved in accelerating the pace of apoptosis.

It is to be expected that as the disease progresses, more and more plaques will be formed, filling more and more of the brain. Studies suggest that it may be that the Aβ is aggregating and disaggregating at the same time, in a sort of dynamic equilibrium. This raises the hope that it may be possible to break down the plaques even after they have formed. (National Institute on Aging Progress Report on Alzheimer's Disease, 1999).

It is believed that Aβ is toxic to neurons. In tissue culture studies, researchers observed an increase in death of hippocampal neurons cells engineered to over-express mutated forms of human APP compared to neurons over-expressing the normal human APP (Luo et al., 1999).

Furthermore, overexpression or the expression of modified forms of the Aβ protein has in animal models been demonstrated to induce Alzheimer-like symptoms, (Hsiao K. et al., 1998)

Given that increased Aβ generation, its aggregation into plaques, and the resulting neurotoxicity may lead to AD, it is of therapeutic interest to investigate conditions under which Aβ aggregation into plaques might be slowed down or even blocked.

Presenilins

Mutations in presenilin-1 (S-180) account for almost 50% of all cases of early-onset familial AD (FAD). Around 30 mutations have been identified that give rise to AD. The onset of AD varies with the mutations. Mutations in presenilin-2 account for a much smaller part of the cases of FAD, but is still a significant factor. It is not known whether presenilins are involved in sporadic non-familial AD. The function of the presenilins is not known, but they appear to be involved in the processing of APP to give Aβ-42 (the longer stickier form of the peptide, SEQ ID NO: 2, residues 673–714), since AD patients with presenilin mutations have increased levels of this peptide. It is unclear whether the presenilins also have a role in causing the generation of NFT's. Some suggest that presenilins could also have a more direct role in the degeneration of neurons and neuron death. Presenilin-1 is located at chromosome 14 while presenilin-2 is linked to chromosome 1. If a person harbours a mutated version of just one of these genes he or she is almost certain to develop early onset AD.

There is some uncertainty to whether presenilin-1 is identical to the hypothetical gamma-secretase involved in the processing of APP (Naruse et al., 1998).

Apolipoprotein E

Apolipoprotein E is usually associated with cholesterol, but is also found in plaques and tangles of AD brains. While alleles 1–3 do not seem to be involved in AD there is a significant correlation between the presence of the APOE-ϵ4 allele and development of late AD (Strittmatter et al., 1993). It is, however, a risk factor and not a direct cause as is the case for the presenilin and APP mutations and it is not limited to familial AD.

The ways in which the ApoE ϵ4 protein increases the likelihood of developing AD are not known with certainty, but one possible theory is that it facilitates Aβ buildup and this contributes to lowering the age of onset of AD, or the presence or absence of particular APOE alleles may affect the way neurons respond to injury (Buttini et al., 1999).

Also Apo AI has been shown to be amyloigenic. Intact apo AI can itself form amyloid-like fibrils in vitro that are Congo red positive (Am J Pathol 147 (2): 238–244 (August 1995), Wisniewski T, Golabek A A, Kida E, Wisniewski K E, Frangione B).

There seem to be some contradictory results indicating that there is a positive effect of the APOE-ϵ4 allele in decreasing symptoms of mental loss, compared to other alleles (Stern, Brandt, 1997, Annals of Neurology 41).

Neurofibrillary Tangles

This second hallmark of AD consists of abnormal collections of twisted threads found inside nerve cells. The chief component of tangles is one form of a protein called tau (τ). In the central nervous system, tau proteins are best known for their ability to bind and help stabilize microtubules, which are one constituent of the cell's internal support structure, or skeleton. However, in AD tau is changed chemically, and this altered tau can no longer stabilize the microtubules, causing them to fall disintegrate. This collapse of the transport system may at first result in malfunctions in communication between nerve cells and may later lead to neuronal death.

In AD, chemically altered tau twists into paired helical filaments—two threads of tau that are wound around each other. These filaments are the major substance found in neurofibrillary tangles. In one recent study, researchers found neurofibrillary changes in fewer than 6 percent of the neurons in a particular part of the hippocampus in healthy brains, in more than 43 percent of these neurons in people who died with mild AD, and in 71 percent of these neurons in people who died with severe AD. When the loss of neurons was studied, a similar progression was found. Evidence of this type supports the idea that the formation of tangles and the loss of neurons progress together over the course of AD. (National Institute on Aging Progress Report on Alzheimer's Disease, 1999).

Tauopathies and Tangles

Several neurodegenerative diseases, other than AD, are characterized by the aggregation of tau into insoluble filaments in neurons and glia, leading to dysfunction and death. Very recently, several groups of researchers, who were studying families with a variety of hereditary dementias other than AD, found the first mutations in the tau gene on chromosome 17 (Clark et al., 1998; Hutton et al., 1998; Poorkaj et al., 1998; Spillantini et al., 1998). In these families, mutations in the tau gene cause neuronal cell death and dementia. These disorders which share some characteristics with AD but differ in several important respects, are collectively called "fronto temporal dementia and parkinsonism linked to chromosome 17" (FTDP-17). They are diseases such as Parkinson's disease, some forms of amyotrophic lateral sclerosis (ALS), corticobasal degeneration, progressive supranuclear palsy, and Pick's disease, and are all characterized by abnormal aggregation of tau protein.

Other AD-like Neurological Diseases.

There are important parallels between AD and other neurological diseases, including prion diseases (such as kuru, Creutzfeld-Jacob disease and bovine spongiform encephalitis), Parkinson's disease, Huntington's disease, and fronto-temporal dementia. All involve deposits of abnormal proteins in the brain. AD and prion diseases cause dementia and death, and both are associated with the formation of insoluble amyloid fibrils, but from membrane proteins that are different from each other.

Scientists studying Parkinson's disease, the second most common neurodegenerative disorder after AD, discovered the first gene linked to the disease. This gene codes for a protein called synuclein, which, intriguingly, is also found in the amyloid plaques of AD patients' brains (Lavedan C, 1998, Genome Res. 8(9): 871–80). Investigators have also discovered that genetic defects in Huntington's disease, another progressive neurodegenerative disorder that causes dementia, cause the Huntington protein to form into insoluble fibrils very similar to the Aβ fibrils of AD and the protein fibrils of prion disease, (Scherzinger E, et al., 1999, PNAS U.S.A. 96(8): 4604–9).

Scientists have also discovered a novel gene, which when mutated, is responsible for familial British dementia (FBD), a rare inherited disease that causes severe movement disorders and progressive dementia similar to that seen in AD. In a biochemical analysis of the amyloid fibrils found in the FBD plaques, a unique peptide named ABri was found (Vidal et al., 1999). A mutation at a particular point along this gene results in the production of a longer-than-normal Bri protein. The ABri peptide, which is snipped from the mutated end of the Bri protein is deposited as amyloid fibrils. These plaques are thought to lead to the neuronal dysfunction and dementia that characterizes FBD.

Immunization with Aβ

The immune system will normally take part in the clearing of foreign protein and proteinaceous particles in the organism but the deposits associated with the above-mentioned diseases consist mainly of self-proteins, thereby rendering the role of the immune system in the control of these diseases less obvious. Further, the deposits are located in a compartment (the CNS) normally separated from the immune system, both facts suggesting that any vaccine or immunotherapeutical approach would be unsuccessful.

Nevertheless, scientists have recently attempted immunizing mice with a vaccine composed of heterologous human Aβ and a substance known to excite the immune system (Schenk et al., 1999 and WO 99/27944). The vaccine was tested in a partial transgenic mouse model of AD with a human mutated gene for APP inserted into the DNA of the mouse. The mice produced the modified APP protein and developed amyloid plaques as they grew older. This mouse model was used to test whether vaccination against the modified transgenic human APP had an effect on plaque build-up. In a first experiment, one group of transgenic mice was given monthly injections of the vaccine starting at 6 weeks of age and ending at 11 months. A second group of transgenic mice received no injections and served as a control group. By 13 months of age, the mice in the control group had plaques covering 2 to 6 percent of their brains. In contrast, the immunized mice had virtually no plaques.

In a second experiment, the researchers began the injections at 11 months, when some plaques had already developed. Over a 7-month period, the control transgenic mice had a 17-fold increase in the amount of plaque in their brains, whereas those who received the vaccine had a 99-percent decrease compared to the 18-month-old control transgenic mice. In some mice, some of the pre-existing plaque deposits appeared to have been removed by the treatment. It was also found that other plaque-associated damage, such as inflammation and abnormal nerve cell processes, lessened as a result of the immunization.

The above is thus a preliminary study in mice and for example, scientists need to find out whether vaccinated mice remain healthy in other respects and whether memory of those vaccinated remains normal. Furthermore, because the mouse model is not a complete representation of AD (the animals do not develop neurofibrillary tangles nor do many of their neurons die), additional studies will be necessary to determine whether humans have a similar or different reaction from mice. Another issue to consider is that the method may perhaps "cure" amyloid deposition but fail to stop development of dementia.

Technical issues present major challenges as well. For example it is unlikely that it is even possible, using this technology, to create a vaccine which enables humans to raise antibodies against their own proteins. So numerous issues of safety and effectiveness will need to be resolved before any tests in humans can be considered.

The work by Schenk et al. thus shows that if it was possible to generate a strong immune response towards self-proteins in proteinaceous deposits in the central nervus system such as the plaques formed in AD, it is possible to both prevent the formation of the deposits and possibly also clear already formed plaques.

OBJECT OF THE INVENTION

The object of the present invention is to provide novel therapies against conditions characterized by deposition of amyloid, such as AD. A further object is to develop an autovaccine against amyloid, in order to obtain a novel treatment for AD and for other pathological disorders involving amyloid deposition.

SUMMARY OF THE INVENTION

Described herein is the use of an autovaccination technology for generating strong immune responses against otherwise non-immunogenic self-proteins included in pathology-related amyloid deposits. Thereby, a strong immune response is generated against either the amyloid, against one or more of the components included in the deposits, or against one or more of the proteins responsible for amyloid formation. Described is also the preparation of such vaccines for the prevention, possible cure or alleviation of the symptoms of such diseases associated with amyloid deposits.

Thus, in its broadest and most general scope, the present invention relates to a method for in vivo down-regulation of amyloid in an animal, including a human being, the method comprising effecting presentation to the animal's immune system of an immunologically effective amount of

- at least one amyloidogenic polypeptide or subsequence thereof which has been formulated so that immunization of the animal with the amyloidogenic polypeptide or subsequence thereof induces production of antibodies against the amyloidogenic polypeptide, and/or
- at least one amyloid analogue wherein is introduced a modification in the amyloidogenic polypeptide which has as a result that immunization of the animal with the analogue induces production of antibodies against the amyloidogenic polypeptide.

Hence, encompassed by the present invention is the use of 1) naturally occurring antigens and fragments thereof formulated so as to trigger an immune response as well as of 2) analogues of such naturally occurring antigens, the analogues being capable of inducing cross-reactive immune responses.

The invention also relates to analogues of the amyloidogenic polypeptides as well as to nucleic acid fragments encoding a subset of these. Also immunogenic compositions comprising the analogues or the nucleic acid fragments are part of the invention.

The invention also relates to a method of identifying immunogenically effective analogues of amyloidogenic polypeptides as well as a method for preparing a composition comprising the analogues.

DETAILED DISCLOSURE OF THE INVENTION

Definitions

Figure 1:
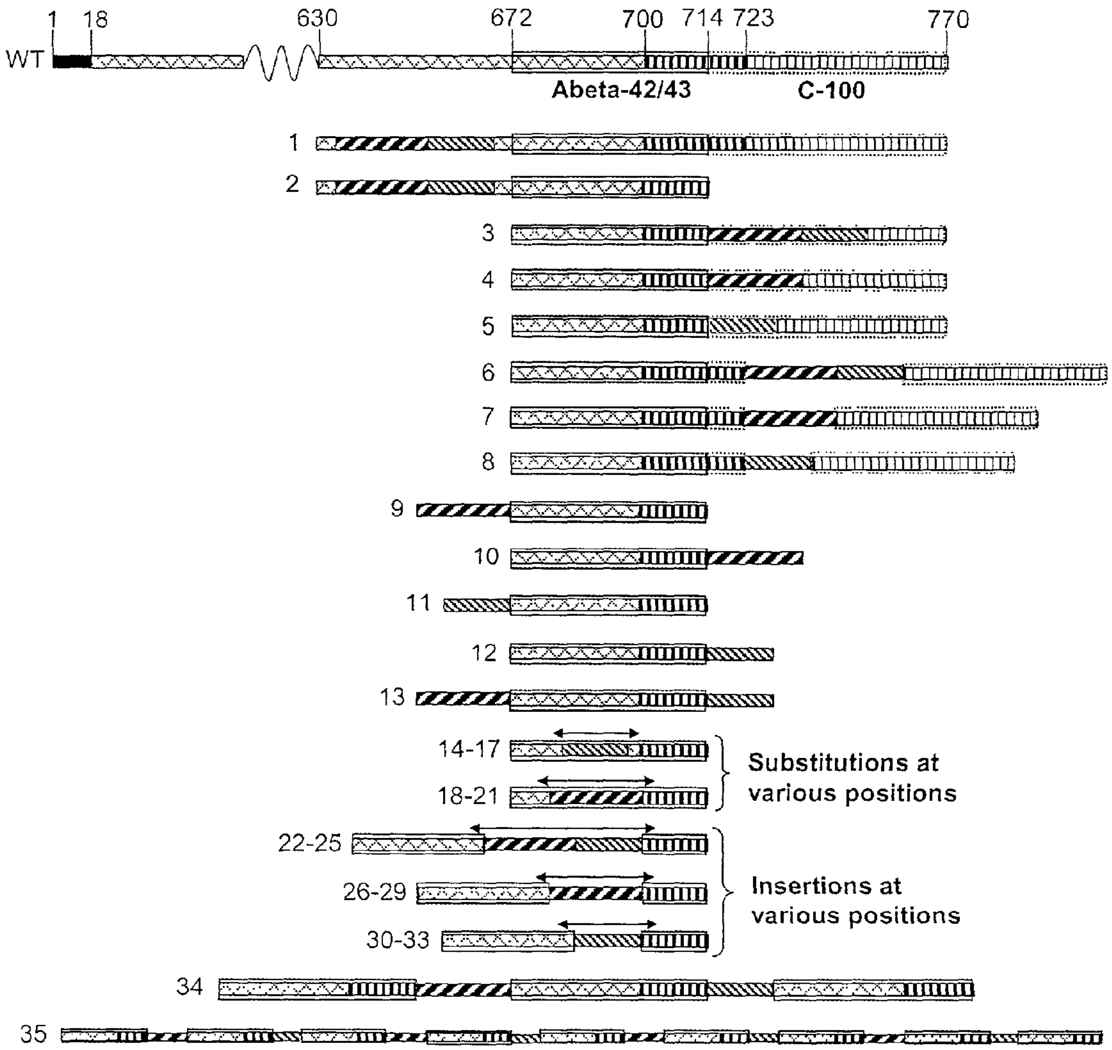
FIG. 1: Schematic depiction of Autovac variants derived from the amyloid precursor protein with the purpose of generating antibody responses against the Aβ protein Aβ-43 (or C-100). The APP is shown schematically at the top of the figure and the remaining schematic constructs show that the model epitopes P2 and P30 are substituted or inserted into various truncations of APP. In the figure, the black pattern indicates the APP signal sequence, two-way cross-hatching is the extracellular part of APP, dark vertical hatching is the transmembrane domain of APP, light vertical hatching is the intracellular domain of APP, coarse cross-hatching indicates the P30 epitope, and fine cross-hatching indicates the P2 epitope. The full line box indicates Aβ-42/43 and the full-line box and the dotted line box together indicate C-100. "Abeta" denotes Aβ.

In the following a number of terms used in the present specification and claims will be defined and explained in detail in order to clarify the metes and bounds of the invention.

The terms "amyloid" and "amyloid protein" which are used interchangeably herein denote a class of proteinaceous unbranched fibrils of indeterminate length. Amyloid fibrils display characteristic staining with Congo Red and share a cross-β structure in which the polypeptide chain is organized in β-sheets. Amyloid is generally derived from amyloidogenic proteins which have very different precursor structures but which can all undergo a structural conversion to a misfolded form that is the building block of the β-sheet helix protofilament. Normally, the diameter of amyloid fibrils varies between about 70 to about 120 Å.

The term "amyloidogenic protein" is intended to denote a polypeptide which is involved in the formation of amyloid deposits, either by being part of the deposits as such or by being part of the biosynthetic pathway leading to the formation of the deposits. Hence, examples of amyloidogenic proteins are APP and Aβ, but also proteins involved in the metabolism of these may be amyloidogenic proteins. A number of amyloidogenic polypeptides are discussed in detail herein.

An "amyloid polypeptide" is herein intended to denote polypeptides comprising the amino acid sequence of the above-discussed amyloidogenic proteins derived from humans or other mammals (or truncates thereof sharing a substantial amount of B-cell epitopes with an intact amyloidogenic protein)—an amyloidogenic polypeptide can therefore e.g. comprise substantial parts of a precursor for the amyloidogenic polypeptide (in the case of Aβ, one possible amyloid polypeptide could be APP derived). Also unglycosylated forms of amyloidogenic polypeptides which are prepared in prokaryotic system are included within the boundaries of the term as are forms having varying glycosylation patterns due to the use of e.g. yeasts or other non-mammalian eukaryotic expression systems. It should, however, be noted that when using the term "an amyloidogenic polypeptide" it is intended that the polypeptide in question is normally non-immunogenic when presented to the animal to be treated. In other words, the amyloidogenic polypeptide is a self-protein or is an analogue of such a self-protein which will not normally give rise to an immune response against the amyloidogenic of the animal in question.

An "analogue of an amyloidogenic polypeptide" is an amyloidogenic polypeptide, which has been subjected to changes in its primary structure. Such a change can e.g. be in the form of fusion of an amyloid polypeptide to a suitable fusion partner (i.e. a change in primary structure exclusively involving C- and/or N-terminal additions of amino acid residues) and/or it can be in the form of insertions and/or deletions and/or substitutions in the amyloidogenic polypeptide's amino acid sequence. Also encompassed by the term are derivatized amyloidogenic molecules, cf. the discussion below of modifications of amyloidogenic polypeptides. In case the amyloidogenic polypeptide is an amyloid or a precursor therefore, the analogue may be constructed so as to be less able or even unable to elicit antibodies against the normal precursor protein(s) of the amyloid, thereby avoiding undesired interference with the (physiologically normal) non-aggregated form of the polypeptide being a precursor of the amyloid protein.

It should be noted that the use as a vaccine in a human of a xeno-analogue (e.g. a canine or porcine analogue) of a human amyloidogenic polypeptide can be imagined to produce the desired immunity against the amyloidogenic polypeptide. Such use of an xeno-analogue for immunization is also considered part of the invention.

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The terms "T-lymphocyte" and "T-cell" will be used interchangeably for lymphocytes of thymic origin which are responsible for various cell mediated immune responses as well as for helper activity in the humoral immune response. Likewise, the terms "B-lymphocyte" and "B-cell" will be used interchangeably for antibody-producing lymphocytes.

The term "subsequence" means any consecutive stretch of at least 3 amino acids or, when relevant, of at least 3 nucleotides, derived directly from a naturally occurring amyloid amino acid sequence or nucleic acid sequence, respectively.

The term "animal" is in the present context in general intended to denote an animal species (preferably mammalian), such as *Homo sapiens, Canis domesticus,* etc. and not just one single animal. However, the term also denotes a population of such an animal species, since it is important that the individuals immunized according to the method of the invention all harbour substantially the same amyloidogenic polypeptide allowing for immunization of the animals with the same immunogen(s). If, for instance, genetic variants of the amyloidogenic polypeptide exists in different human population it may be necessary to use different immunogens in these different populations in order to be able to break the autotolerance towards the amyloidogenic polypeptide in each population in an optimum fashion. It will be clear to the skilled person that an animal in the present context is a living being which has an immune system. It is preferred that the animal is a vertebrate, such as a mammal.

By the term "in vivo down-regulation of amyloid" is herein meant reduction in the living organism of the total amount of deposited amyloid of the relevant type. The down-regulation can be obtained by means of several mechanisms: Of these, simple interference with amyloid by antibody binding so as to prevent misaggregation is the most simple. However, it is also within the scope of the present invention that the antibody binding results in removal of amyloid by scavenger cells (such as macrophages and other phagocytic cells) and that the antibodies interfer with other amyloidogenic polypeptides which lead to amyloid formation.

The expression "effecting presentation . . . to the immune system" is intended to denote that the animal's immune system is subjected to an immunogenic challenge in a controlled manner. As will appear from the disclosure below, such challenge of the immune system can be effected in a number of ways of which the most important are vaccination with polypeptide containing "pharmaccines" (i.e. a vaccine which is administered to treat or ameliorate ongoing disease) or nucleic acid "pharmaccine" vaccination. The important result to achieve is that immune competent cells in the animal are confronted with the antigen in an immunologically effective manner, whereas the precise mode of achieving this result is of less importance to the inventive idea underlying the present invention.

The term "immunogenically effective amount" has its usual meaning in the art, i.e. an amount of an immunogen, which is capable of inducing an immune response that significantly engages pathogenic agents sharing immunological features with the immunogen.

When using the expression that the amyloidogenic polypeptide has been "modified" is herein meant a chemical modification of the polypeptide, which constitutes the backbone of the amyloidogenic polypeptide. Such a modification can e.g. be derivatization (e.g. alkylation) of certain amino acid residues in the sequence of the amyloidogenic polypeptide, but as will be appreciated from the disclosure below, the preferred modifications comprise changes of the primary structure of the amino acid sequence.

When discussing "autotolerance towards an amyloidogenic polypeptide" it is understood that since the amyloidogenic polypeptide is a self-protein in the population to be vaccinated, normal individuals in the population do not mount an immune response against the amyloidogenic polypeptide; it cannot be excluded, though, that occasional individuals in an animal population might be able to produce antibodies against native amyloidogenic polypeptide, e.g. as part of an autoimmune disorder. At any rate, an animal will normally only be autotolerant towards its own amyloidogenic polypeptide, but it cannot be excluded that analogues derived from other animal species or from a population having a different phenotype would also be tolerated by said animal.

A "foreign T-cell epitope" (or: "foreign T-lymphocyte epitope") is a peptide which is able to bind to an MHC molecule and which stimulates T-cells in an animal species. Preferred foreign T-cell epitopes in the invention are "promiscuous" epitopes, i.e. epitopes which bind to a substantial fraction of a particular class of MHC molecules in an animal species or population. Only a very limited number of such promiscuous T-cell epitopes are known, and they will be discussed in detail below. Promiscuous T-cell epitopes are also denoted "universal" T-cell epitopes. It should be noted that in order for the immunogens which are used according to the present invention to be effective in as large a fraction of an animal population as possible, it may be necessary to 1) insert several foreign T-cell epitopes in the same analogue or 2) prepare several analogues wherein each analogue has a different promiscuous epitope inserted. It should be noted also that the concept of foreign T-cell epitopes also encompasses use of cryptic T-cell epitopes, i.e. epitopes which are derived from a self-protein and which only exerts immunogenic behaviour when existing in isolated form without being part of the self-protein in question.

A "foreign T helper lymphocyte epitope" (a foreign $T_H$ epitope) is a foreign T cell epitope, which binds an MHC Class II molecule and can be presented on the surface of an antigen presenting cell (APC) bound to the MHC Class II molecule.

A "functional part" of a (bio)molecule is in the present context intended to mean the part of the molecule which is responsible for at least one of the biochemical or physiological effects exerted by the molecule. It is well-known in the art that many enzymes and other effector molecules have an active site which is responsible for the effects exerted by the molecule in question. Other parts of the molecule may serve a stabilizing or solubility enhancing purpose and can therefore be left out if these purposes are not of relevance in the context of a certain embodiment of the present invention. For instance it is possible to use certain cytokines as a modifying moiety in an amyloidogenic polypeptide (cf. the detailed discussion below), and in such a case, the issue of stability may be irrelevant since the coupling to the amyloidogenic polypeptide may provide the stability necessary.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Targeting" of a molecule is in the present context intended to denote the situation where a molecule upon introduction in the animal will appear preferentially in certain tissue(s) or will be preferentially associated with certain cells or cell types. The effect can be accomplished in a number of ways including formulation of the molecule in composition facilitating targeting or by introduction in the molecule of groups, which facilitate targeting. These issues will be discussed in detail below.

"Stimulation of the immune system" means that a substance or composition of matter exhibits a general, non-specific immunostimulatory effect. A number of adjuvants and putative adjuvants (such as cytokines) share the ability to stimulate the immune system. The result of using an immunostimulating agent is an increased "alertness" of the immune system meaning that simultaneous or subsequent immunization with an immunogen induces a significantly more effective immune response compared to the isolated use of the immunogen Preferred Embodiments of Amyloid Down-regulation It is preferred that the amyloidogenic polypeptide used as an immunogen in the method of the invention is a modified molecule wherein at least one change is present in the amino acid sequence of the amyloidogenic polypeptide, since the chances of obtaining the all-important breaking of autotolerance towards the amyloidogenic polypeptide is greatly facilitated that way—this is e.g. evident from the results presented in Example 2 herein, where immunization with wild-type Aβ is compared to immunization with an Aβ variant molecule. It should be noted that the use of a modified molecule does not exclude the possibility of using such a modified amyloidogenic polypeptide in formulations which further facilitate the breaking of autotolerance against the amyloidogenic polypeptide, e.g. formulations containing adjuvants.

It has been shown (in Dalum I et al., 1996, J. Immunol. 157: 4796–4804) that potentially self-reactive B-lymphocytes recognizing self-proteins are physiologically present in normal individuals. However, in order for these B-lymphocytes to be induced to actually produce antibodies reactive with the relevant self-proteins, assistance is needed from cytokine producing T-helper lymphocytes ($T_H$-cells or $T_H$-lymphocytes). Normally this help is not provided because T-lymphocytes in general do not recognize T-cell epitopes derived from self-proteins when presented by antigen presenting cells (APCs). However, by providing an element of "foreignness" in a self-protein (i.e. by introducing an immunologically significant modification), T-cells recognizing the foreign element are activated upon recognizing the foreign epitope on an APC (such as, initially, a mononuclear cell). Polyclonal B-lymphocytes (which are also APCs) capable of recognising self-epitopes on the modified self-protein also internalise the antigen and subsequently presents the foreign T-cell epitope(s) thereof, and the activated T-lymphocytes subsequently provide cytokine help to these self-reactive polyclonal B-lymphocytes. Since the antibodies produced by these polyclonal B-lymphocytes are reactive with different epitopes on the modified polypeptide, including those which are also present in the native polypeptide, an antibody cross-reactive with the non-modified self-protein is induced. In conclusion, the T-lymphocytes can be led to act as if the population of polyclonal B-lymphocytes have recognised an entirely foreign antigen, whereas in fact only the inserted epitope(s) is/are foreign to the host. In this way, antibodies capable of cross-reacting with non-modified self-antigens are induced.

Several ways of modifying a peptide self-antigen in order to obtain breaking of autotolerance are known in the art. Hence, according to the invention, the modification can include that

- at least one foreign T-cell epitope is introduced, and/or
- at least one first moiety is introduced which effects targeting of the modified molecule to an antigen presenting cell (APC), and/or
- at least one second moiety is introduced which stimulates the immune system, and/or
- at least one third moiety is introduced which optimizes presentation of the modified amyloidogenic polypeptide to the immune system.

However, all these modifications should be carried out while maintaining a substantial fraction of the original B-lymphocyte epitopes in the amyloidogenic polypeptide, since the B-lymphocyte recognition of the native molecule is thereby enhanced.

In one preferred embodiment, side groups (in the form of foreign T-cell epitopes or the above-mentioned first, second and third moieties) are covalently or non-covalently introduced. This is to mean that stretches of amino acid residues derived from the amyloidogenic polypeptide are derivatized without altering the primary amino acid sequence, or at least without introducing changes in the peptide bonds between the individual amino acids in the chain.

An alternative, and preferred, embodiment utilises amino acid substitution and/or deletion and/or insertion and/or addition (which may be effected by recombinant means or by means of peptide synthesis; modifications which involves longer stretches of amino acids can give rise to fusion polypeptides). One especially preferred version of this embodiment is the technique described in WO 95/05849, which discloses a method for down-regulating self-proteins by immunising with analogues of the self-proteins wherein a number of amino acid sequencers) has been substituted with a corresponding number of amino acid sequence(s) which each comprise a foreign immunodominant T-cell epitope, while at the same time maintaining the overall tertiary structure of the self-protein in the analogue. For the purposes of the present invention, it is however sufficient if the modification (be it an insertion, addition, deletion or substitution) gives rise to a foreign T-cell epitope and at the same time preserves a substantial number of the B-cell epitopes in the amyloidogenic polypeptide. However, in order to obtain maximum efficacy of the immune response induced, it is preferred that the overall tertiary structure of the amyloidogenic polypeptide is maintained in the modified molecule.

The following formula describes the molecular constructs generally covered by the invention:

$$(MOD_1)_{s1}(\text{amyloid}_{e1})_{n1}(MOD_2)_{s2}(\text{amyloid}_{e2})_{n2} \ldots (MOD_x)_{sx}(\text{amyloid}_{ex})_{nx} \qquad (I)$$

where amyloid$_{e1}$-amyloid$_{ex}$ are x B-cell epitope containing subsequences of an amyloidogenic polypeptide which independently are identical or non-identical and which may contain or not contain foreign side groups, x is an integer $\geqq 3$, n1−nx are x integers $\geqq 0$ (at least one is $\geqq 1$), MOD$_1$-MOD$_x$ are x modifications introduced between the preserved B-cell epitopes, and $s_1$-$s_x$ are x integers$\geqq 0$ (at least one is $\geqq 1$ if no side groups are introduced in the amyloid$_{ex}$ sequences) Thus, given the general functional restraints on the immunogenicity of the constructs, the invention allows for all kinds of permutations of the original sequence of the amyloidogenic polypeptide, and all kinds of modifications therein. Thus, included in the invention are modified amyloidogenic polypeptides obtained by omission of parts of the sequence of the amyloidogenic polypeptide which e.g. exhibit adverse effects in vivo or omission of parts which are normally intracellular and thus could give rise to undesired immunological reactions.

One preferred version of the constructs outlined above are, when applicable, those where the B-cell epitope containing subsequence of an amyloid protein is not extracellularly exposed in the precursor polypeptide from which the amyloid is derived. By making such a choice of the amyloid epitopes, it is ensured that antibodies are not generated which would be reactive with the cells producing the amyloid precursor and thereby the immune response which is generated becomes limited to an immune response against the undesired amyloid deposits. A similar choice can, when applicable, be made for other amyloidogenic polypeptides than amyloid. In these cases it will e.g. be feasible to induce immunity against epitopes of the amyloidogenic polypeptide which are only exposed to the extracellular phase when being free from any coupling to the cells from which they are produced.

Maintenance of a substantial fraction of B-cell epitopes or even the overall tertiary structure of a protein which is subjected to modification as described herein can be achieved in several ways. One is simply to prepare a polyclonal anti-serum directed against the amyloidogenic polypeptide (e.g. an antiserum prepared in a rabbit) and thereafter use this antiserum as a test reagent (e.g. in a competitive ELISA) against the modified proteins which are produced. Modified versions (analogues) which react to the same extent with the antiserum as does the amyloidogenic polypeptide must be regarded as having the same overall tertiary structure as the amyloidogenic polypeptide whereas analogues exhibiting a limited (but still significant and specific) reactivity with such an antiserum are regarded as having maintained a substantial fraction of the original B-cell epitopes.

Alternatively, a selection of monoclonal antibodies reactive with distinct epitopes on the amyloidogenic polypeptide can be prepared and used as a test panel. This approach has the advantage of allowing 1) an epitope mapping of the amyloidogenic polypeptide and 2) a mapping of the epitopes which are maintained in the analogues prepared.

Of course, a third approach would be to resolve the 3-dimensional structure of the amyloidogenic polypeptide or of a biologically active truncate thereof (cf. above) and compare this to the resolved three-dimensional structure of the analogues prepared. Three-dimensional structure can be resolved by the aid of X-ray diffraction studies and NMR-spectroscopy. Further information relating to the tertiary structure can to some extent be obtained from circular dichroism studies which have the advantage of merely requiring the polypeptide in pure form (whereas X-ray diffraction requires the provision of crystallized polypeptide and NMR requires the provision of isotopic variants of the polypeptide) in order to provide useful information about the tertiary structure of a given molecule. However, ultimately X-ray diffraction and/or NMR are necessary to obtain conclusive data since circular dichroism can only provide indirect evidence of correct 3-dimensional structure via information of secondary structure elements.

One preferred embodiment of the invention utilises multiple presentations of B-lymphocyte epitopes of the amyloidogenic polypeptide (i.e. formula I wherein at least one B-cell epitope is present in two positions). This effect can be achieved in various ways, e.g. by simply preparing fusion polypeptides comprising the structure (amyloidogenic polypeptide)$_m$ where m is an integer ≧2 and then introduce the modifications discussed herein in at least one of the amyloid sequences. It is preferred that the modifications introduced includes at least one duplication of a B-lymphocyte epitope and/or the introduction of a hapten. These embodiments including multiple presentations of selected epitopes are especially preferred in situations where merely minor parts of the amyloidogenic polypeptide are useful as constituents in a vaccine agent.

As mentioned above, the introduction of a foreign T-cell epitope can be accomplished by introduction of at least one amino acid insertion, addition, deletion, or substitution. Of course, the normal situation will be the introduction of more than one change in the amino acid sequence (e.g. insertion of or substitution by a complete T-cell epitope) but the important goal to reach is that the analogue, when processed by an antigen presenting cell (APC), will give rise to such a foreign immunodominant T-cell epitope being presented in context of an MCH Class II molecule on the surface of the APC. Thus, if the amino acid sequence of the amyloidogenic polypeptide in appropriate positions comprises a number of amino acid residues which can also be found in a foreign $T_H$ epitope then the introduction of a foreign $T_H$ epitope can be accomplished by providing the remaining amino acids of the foreign epitope by means of amino acid insertion, addition, deletion and substitution. In other words, it is not necessary to introduce a complete $T_H$ epitope by insertion or substitution in order to fulfill the purpose of the present invention.

It is preferred that the number of amino acid insertions, deletions, substitutions or additions is at least 2, such as 3, 4, 5, 6, 7, 8, 9, 10, 11, 12, 13, 14, 15, 16, 17, 18, 19, 20, and 25 insertions, substitutions, additions or deletions. It is furthermore preferred that the number of amino acid insertions, substitutions, additions or deletions is not in excess of 150, such as at most 100, at most 90, at most 80, and at most 70. It is especially preferred that the number of substitutions, insertions, deletions, or additions does not exceed 60, and in particular the number should not exceed 50 or even 40. Most preferred is a number of not more than 30. With respect to amino acid additions, it should be noted that these, when the resulting construct is in the form of a fusion polypeptide, is often considerably higher than 150.

Preferred embodiments of the invention includes modification by introducing at least one foreign immunodominant T-cell epitope. It will be understood that the question of immune dominance of a T-cell epitope depends on the animal species in question. As used herein, the term "immunodominance" simply refers to epitopes which in the vaccinated individual/population gives rise to a significant immune response, but it is a well-known fact that a T-cell epitope which is immunodominant in one individual/population is not necessarily immunodominant in another individual of the same species, even though it may be capable of binding MHC-II molecules in the latter individual. Hence, for the purposes of the present invention, an immune dominant T-cell epitope is a T-cell epitope which will be effective in providing T-cell help when present in an antigen. Typically, immune dominant T-cell epitopes has as an inherent feature that they will substantially always be presented bound to an MHC Class II molecule, irrespective of the polypeptide wherein they appear.

Another important point is the issue of MHC restriction of T-cell epitopes. In general, naturally occurring T-cell epitopes are MHC restricted, i.e. a certain peptides constituting a T-cell epitope will only bind effectively to a subset of MHC Class II molecules. This in turn has the effect that in most cases the use of one specific T-cell epitope will result in a vaccine component which is only effective in a fraction of the population, and depending on the size of that fraction, it can be necessary to include more T-cell epitopes in the same molecule, or alternatively prepare a multi-component vaccine wherein the components are variants of the amyloidogenic polypeptide which are distinguished from each other by the nature of the T-cell epitope introduced.

If the MHC restriction of the T-cells used is completely unknown (for instance in a situation where the vaccinated animal has a poorly defined MHC composition), the fraction of the population covered by a specific vaccine composition can be determined by means of the following formula $$f_{population} = 1 - \prod_{i=1}^{n} (1 - p_i) \qquad \text{(II)}$$

where $p_1$ is the frequency in the population of responders to the $i^{th}$ foreign T-cell epitope present in the vaccine composition, and n is the total number of foreign T-cell epitopes in the vaccine composition. Thus, a vaccine composition containing 3 foreign T-cell epitopes having response frequencies in the population of 0.8, 0.7, and 0.6, respectively, would give $$1-0.2\times0.3\times0.4=0.976$$

i.e. 97.6 percent of the population will statistically mount an MHC-II mediated response to the vaccine.

The above formula does not apply in situations where a more or less precise MHC restriction pattern of the peptides used is known. If, for instance a certain peptide only binds the human MHC-II molecules encoded by HLA-DR alleles DR1, DR3, DR5, and DR7, then the use of this peptide together with another peptide which binds the remaining MHC-II molecules encoded by HLA-DR alleles will accomplish 100% coverage in the population in question. Likewise, if the second peptide only binds DR3 and DRS, the addition of this peptide will not increase the coverage at all. If one bases the calculation of population response purely on MHC restriction of T-cell epitopes in the vaccine, the fraction of the population covered by a specific vaccine composition can be determined by means of the following formula:

$$f_{population} = 1 - \prod_{i=1}^{3} (1 - \varphi_i)^2 \quad \text{(III)}$$

wherein $\phi_j$ is the sum of frequencies in the population of allelic haplotypes encoding MHC molecules which bind any one of the T-cell epitopes in the vaccine and which belong to the $j^{th}$ of the 3 known HLA loci (DP, DR and DQ); in practice, it is first determined which MHC molecules will recognize each T-cell epitope in the vaccine and thereafter these are listed by type (DP, DR and DQ)—then, the individual frequencies of the different listed allelic haplotypes are summed for each type, thereby yielding $\phi_1$, $\phi_2$, and $\phi_3$.

It may occur that the value $p_i$ in formula II exceeds the corresponding theoretical value $\pi_i$:

$$\pi_i = 1 - \prod_{i=1}^{3} (1 - \nu_i)^2 \quad \text{(IV)}$$

wherein $U_j$ is the sum of frequencies in the population of allelic haplotype encoding MHC molecules which bind the $i^{th}$ T-cell epitope in the vaccine and which belong to the $j^{th}$ of the 3 known HLA loci (DP, DR and DQ). This means that in $1-\pi_i$ of the population is a frequency of responders of $f_{residual\_i}=(p_i-\pi_i)/(1-\pi_i)$. Therefore, formula III can be adjusted so as to yield formula V:

$$f_{population} = 1 - \prod_{i=1}^{3} (1 - \varphi_i)^2 + \left(1 - \prod_{i=1}^{n} (1 - f_{residual\_i})\right) \quad \text{(V)}$$

where the term $1-f_{residual-i}$ is set to zero if negative. It should be noted that formula V requires that all epitopes have been haplotype mapped against identical sets of haplotypes.

Therefore, when selecting T-cell epitopes to be introduced in the analogue, it is important to include all knowledge of the epitopes which is available: 1) The frequency of responders in the population to each epitope, 2) MHC restriction data, and 3) frequency in the population of the relevant haplotypes.

There exist a number of naturally occurring "promiscuous" T-cell epitopes which are active in a large proportion of individuals of an animal species or an animal population and these are preferably introduced in the vaccine thereby reducing the need for a very large number of different analogues in the same vaccine.

The promiscuous epitope can according to the invention be a naturally occurring human T-cell epitope such as epitopes from tetanus toxoid (e.g. the P2 and P30 epitopes), diphtheria toxoid, Influenza virus hemagluttinin (HA), and *P. falciparum* CS antigen.

Over the years a number of other promiscuous T-cell epitopes have been identified. Especially peptides capable of binding a large proportion of HLA-DR molecules encoded by the different HLA-DR alleles have been identified and these are all possible T-cell epitopes to be introduced in the analogues used according to the present invention. Cf. also the epitopes discussed in the following references which are hereby all incorporated by reference herein: WO 98/23635 (Frazer I H et al., assigned to The University of Queensland); Southwood S et. al, 1998, J. Immunol. 160: 3363–3373; Sinigaglia F et al., 1988, Nature 336: 778–780; Chicz R M et al., 1993, J. Exp. Med 178: 27–47; Hammer J et al., 1993, Cell 74: 197–203; and Falk K et al., 1994, Immunogenetics 39: 230–242. The latter reference also deals with HLA-DQ and -DP ligands. All epitopes listed in these 5 references are relevant as candidate natural epitopes to be used in the present invention, as are epitopes which share common motifs with these.

Alternatively, the epitope can be any artificial T-cell epitope which is capable of binding a large proportion of MHC Class II molecules. In this context the pan DR epitope peptides ("PADRE") described in WO 95/07707 and in the corresponding paper Alexander J et al., 1994, Immunity 1: 751–761 (both disclosures are incorporated by reference herein) are interesting candidates for epitopes to be used according to the present invention. It should be noted that the most effective PADRE peptides disclosed in these papers carry D-amino acids in the C- and N-termini in order to improve stability when administered. However, the present invention primarily aims at incorporating the relevant epitopes as part of the modified amyloidogenic polypeptide which should then subsequently be broken down enzymatically inside the lysosomal compartment of APCs to allow subsequent presentation in the context of an MHC-II molecule and therefore it is not expedient to incorporate D-amino acids in the epitopes used in the present invention.

One especially preferred PADRE peptide is the one having the amino acid sequence AKFVAAWTLKAAA (SEQ ID NO: 19) or an immunologically effective subsequence thereof. This, and other eptiopes having the same lack of MHC restriction are preferred T-cell epitopes which should be present in the analogues used in the inventive method. Such super-promiscuous epitopes will allow for the most simple embodiments of the invention wherein only one single modified amyloidogenic polypeptide is presented to the vaccinated animal's immune system.

As mentioned above, the modification of the amyloidogenic polypeptide can also include the introduction of a first moiety which targets the modified amyloidogenic polypeptide to an APC or a B-lymphocyte. For instance, the first moiety can be a specific binding partner for a B-lymphocyte specific surface antigen or for an APC specific surface antigen. Many such specific surface antigens are known in the art. For instance, the moiety can be a carbohydrate for which there is a receptor on the B-lymphocyte or the APC (e.g. mannan or mannose). Alternatively, the second moiety can be a hapten. Also an antibody fragment which specifically recognizes a surface molecule on APCs or lymphocytes can be used as a first moiety (the surface molecule can e.g. be an FCγ receptor of macrophages and monocytes, such as FCγRI or, alternatively any other specific surface marker such as CD40 or CTLA-4). It should be noted that all these exemplary targeting molecules can be used as part of an adjuvant also, cf. below.

As an alternative or supplement to targeting the modified amyloidogenic polypeptide to a certain cell type in order to achieve an enhanced immune response, it is possible to increase the level of responsiveness of the immune system by including the above-mentioned second moiety which stimulates the immune system. Typical examples of such second moieties are cytokines, and heat-shock proteins or molecular chaperones, as well as effective parts thereof.

Suitable cytokines to be used according to the invention are those which will normally also function as adjuvants in a vaccine composition, i.e. for instance interferon γ (IFN-γ) interleukin 1 (IL-1), interleukin 2 (IL-2), interleukin 4 (IL-4), interleukin 6 (IL-6), interleukin 12 (IL-12), interleukin 13 (IL-13), interleukin 15 (IL-15), and granulocyte-macrophage colony stimulating factor (GM-CSF); alternatively, the functional part of the cytokine molecule may suffice as the second moiety. With respect to the use of such cytokines as adjuvant substances, cf. the discussion below.

According to the invention, suitable heat-shock proteins or molecular chaperones used as the second moiety can be HSP70, HSP90, HSC70, GRP94 (also known as gp96, cf. Wearsch P A et al. 1998, Biochemistry 37: 5709–19), and CRT (calreticulin).

Alternatively, the second moiety can be a toxin, such as listeriolycin (LLO), lipid A and heat-labile enterotoxin. Also, a number of mycobacterial derivatives such as MDP (muramyl dipeptide), CFA (complete Freund's adjuvant) and the trehalose diesters TDM and TDE are interesting possibilities.

Also the possibility of introducing a third moiety which enhances the presentation of the modified amyloidogenic polypeptide to the immune system is an important embodiment of the invention. The art has shown several examples of this principle. For instance, it is known that the palmitoyl lipidation anchor in the *Borrelia burgdorferi* protein OspA can be utilised so as to provide self-adjuvating polypeptides (cf. e.g. WO 96/40718)—it seems that the lipidated proteins form up micelle-like structures with a core consisting of the lipidation anchor parts of the polypeptides and the remaining parts of the molecule protruding therefrom, resulting in multiple presentations of the antigenic determinants. Hence, the use of this and related approaches using different lipidation anchors (e.g. a myristyl group, a myristyl group, a farnesyl group, a geranyl-geranyl group, a GPI-anchor, and an N-acyl diglyceride group) are preferred embodiments of the invention, especially since the provision of such a lipidation anchor in a recombinantly produced protein is fairly straightforward and merely requires use of e.g. a naturally occurring signal sequence as a fusion partner for the modified amyloidogenic polypeptide. Another possibility is use of the C3d fragment of complement factor C3 or C3 itself (cf. Dempsey et al., 1996, Science 271, 348–350 and Lou & Kohler, 1998, Nature Biotechnology 16, 458–462).

An alternative embodiment of the invention which also results in the preferred presentation of multiple (e.g. at least 2) copies of the important epitopic regions of the amyloidogenic polypeptide to the immune system is the covalent coupling of the amyloidogenic polypeptide, subsequence or variants thereof to certain molecules. For instance, polymers can be used, e.g. carbohydrates such as dextran, cf. e.g. Lees A et al., 1994, Vaccine 12: 1160–1166; Lees A et al., 1990, J Immunol. 145: 3594–3600, but also mannose and mannan are useful alternative. Integral membrane proteins from e.g. *E. coli* and other bacteria are also useful conjugation partners. The traditional carrier molecules such as keyhole limpet hemocyanin (KLH), tetanus toxoid, diphtheria toxoid, and bovine serum albumin (BSA) are also preferred and useful conjugation partners.

Preferred embodiments of covalent coupling of the amyloidogenic polypeptide to polyhydroxypolymers such as carbohydrates involve the use of at least one amyloidogenic polypeptide and at least one foreign T-helper epitope which are coupled separately to the polyhydroxypolymer (i.e. the foreign T-helper epitope and the amyloidogenic polypeptide are not fused to each other but rather bound to the polyhydroxypolymer which then serves as a carrier backbone). Again, such an embodiment is most preferred when the suitable B-cell epitope carrying regions of the amyloidogenic polypeptide are constituted by short peptide stretches—this is because this approach is one very convenient way to achieve multiple presentations of selected epitopes in the resulting immunogenic agent.

It is especially preferred that the coupling of the foreign T-helper epitope and the amyloidogenic (poly)peptide is by means of an amide bond which can be cleaved by a peptidase. This strategy has the effect that APCs will be able to take up the conjugate and at the same time be able to process the conjugate and subsequently present the foreign T-cell epitope in an MHC Class II context.

One way of achieving coupling of peptides (both the amyloidogenic polypeptide and the foreign epitope) is to activate a suitable polyhydroxypolymer with tresyl groups; it is e.g. possible to prepare tresylated polysaccharides as described in WO 00/05316 and U.S. Pat. No. 5,874,469 (both incorporated by reference herein) and couple these to amyloidogenic peptides and T-cell epitopes prepared by means of conventional solid or liquid phase peptide synthesis techniques. The resulting product consists of a polyhydroxypolymer backbone (e.g. a dextran backbone) that has, attached thereto by their N-termini or by other available nitrogen moieties, amyloidogenic polypeptides and foreign T-cell epitopes. If desired, it is possible to synthesise the amyloidogenic polypeptides so as to protect all available amino groups but the one at the N-terminus, subsequently couple the resulting protected peptides to the tresylated dextran moiety, and finally deprotecting the resulting conjugate. A specific example of this approach is described in the examples below.

Instead of using the water-soluble polysaccharide molecules as taught in WO 00/05316 and U.S. Pat. No. 5,874,469, it is equally possible to utilise cross-linked polysaccharide molecules, thereby obtaining a particulate conjugate between polypeptides and polysaccharide—this is believed to lead to an improved presentation to the immune system of the polypeptides, since two goals are reached, namely to obtain a local deposit effect when injecting the conjugate and to obtain particles which are attractive targets for APCs. The approach of using such particulate systems is also detailed in the examples.

Considerations underlying chosen areas of introducing modifications in amyloidogenic polypeptides are a) preservation of known and predicted B-cell epitopes, b) preservation of tertiary structure, c) avoidance of B-cell epitopes present on "producer cells" etc. At any rate, as discussed above, it is fairly easy to screen a set of modified amyloidogenic molecules which have all been subjected to introduction of a T-cell epitope in different locations.

Since the most preferred embodiments of the present invention involve down-regulation of human Aβ, it is consequently preferred that the amyloid polypeptide discussed above is a human Aβ polypeptide. In this embodiment, it is especially preferred that the human amyloidogenic polypeptide has been modified by substituting at least one amino acid sequence in SEQ ID NO: 2 with at least one amino acid sequence of equal or different length and containing a foreign $T_H$ epitope. Preferred examples of modified amyloidogenic APP and Aβ are shown schematically in FIG. 1 using the P2 and P30 epitopes as examples. The rationale behind such constructs is discussed in detail in the example.

More specifically, a $T_H$ containing (or completing) amino acid sequence which is introduced into SEQ ID NO: 2 may be introduced at any amino acid in SEQ ID NO: 2. That is, the introduction is possible after any of amino acids 1–770, but preferably after any of amino acids 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, and 714 in SEQ ID NO: 2. This may be combined with deletion of any or all of amino acids 1–671, or any of all of amino acids 715–770. Furthermore, when utilising the technique of substitution, any one of amino acids 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, and 714 in SEQ ID NO: 2 may be deleted in combination with the introduction.

Formulation of the Amyloidogenic Polypeptide and Modified Amyloidogenic Polypeptides When effecting presentation of the amyloidogenic polypeptide or the modified amyloidogenic polypeptide to an animal's immune system by means of administration thereof to the animal, the formulation of the polypeptide follows the principles generally acknowledged in the art.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, intradermally, subdermally or intramuscularly. Additional formulations which are suitable for other modes of administration include suppositories and, in some cases, oral, buccal, sublingual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%. For oral formulations, cholera toxin is an interesting formulation partner (and also a possible conjugation partner).

The polypeptides may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 2,000 μg (even though higher amounts in the 1–10 mg range are contemplated), such as in the range from about 0.5 μg to 1,000 μg, preferably in the range from 1 μg to 500 μg and especially in the range from about 10 μg to 100 μg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generationn Immunological Adjuvants", 1995, Gregoriadis G et al. (eds.), Plenum Press, New York, ISBN 0-306-45283-9, both of which are hereby incorporated by reference herein.

It is especially preferred to use an adjuvant which can be demonstrated to facilitate breaking of the autotolerance to autoantigens; in fact, this is essential in cases where unmodified amyloidogenic polypeptide is used as the active ingredient in the autovaccine. Non-limiting examples of suitable adjuvants are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminium adjuvants; DNA adjuvants; γ-inulin; and an encapsulating adjuvant. In general it should be noted that the disclosures above which relate to compounds and agents useful as first, second and third moieties in the analogues also refer mutatis mutandis to their use in the adjuvant of a vaccine of the invention.

The application of adjuvants include use of agents such as aluminum hydroxide or phosphate (alum), commonly used as 0.05 to 0.1 percent solution in buffered saline, admixture with synthetic polymers of sugars (e.g. Carbopol®) used as 0.25 percent solution, aggregation of the protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Admixture with oils such as squalene and IFA is also preferred.

According to the invention DDA (dimethyldioctadecylammonium bromide) is an interesting candidate for an adjuvant as is DNA and γ-inulin, but also Freund's complete and incomplete adjuvants as well as *quillaja saponins* such as QuilA and QS21 are interesting as is RIBI. Further possibilities are monophosphoryl lipid A (MPL), the above mentioned C3 and C3d, and muramyl dipeptide (MDP).

Liposome formulations are also known to confer adjuvant effects, and therefore liposome adjuvants are preferred according to the invention.

Also immunostimulating complex matrix type (ISCOM® matrix) adjuvants are preferred choices according to the invention, especially since it has been shown that this type of adjuvants are capable of up-regulating MHC Class II expression by APCs. An ISCOM® matrix consists of (optionally fractionated) saponins (triterpenoids) from *Quillaja saponaria*, cholesterol, and phospholipid. When admixed with the immunogenic protein, the resulting particulate formulation is what is known as an ISCOM particle where the saponin constitutes 60–70% w/w, the cholesterol and phospholipid 10–15% w/w, and the protein 10–15% w/w. Details relating to composition and use of immunostimulating complexes can e.g. be found in the above-mentioned text-books dealing with adjuvants, but also Morein B et al., 1995, Clin. Immunother. 3: 461–475 as well as Barr IG and Mitchell GF, 1996, Immunol. and Cell Biol. 74: 8–25 (both incorporated by reference herein) provide useful instructions for the preparation of complete immunostimulating complexes.

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fcγ receptors on monocytes/macrophages. Especially conjugates between antigen and anti-FcγRI have been demonstrated to enhance immunogenicity for the purposes of vaccination.

Other possibilities involve the use of the targeting and immune modulating substances (i.a. cytokines) mentioned above as candidates for the first and second moieties in the modified versions of amyloidogenic polypeptides. In this connection, also synthetic inducers of cytokines like poly I:C are possibilities.

Suitable mycobacterial derivatives are selected from the group consisting of muramyl dipeptide, complete Freund's adjuvant, RIBI, and a diester of trehalose such as TDM and TDE.

Suitable immune targeting adjuvants are selected from the group consisting of CD40 ligand and CD40 antibodies or specifically binding fragments thereof (cf. the discussion above), mannose, a Fab fragment, and CTLA-4.

Suitable polymer adjuvants are selected from the group consisting of a carbohydrate such as dextran, PEG, starch, mannan, and mannose; a plastic polymer such as; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T-and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is i.a. described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. $12^{th}$–$15^{th}$ 1998, Seascape Resort, Aptos, Calif.".

Microparticle formulation of vaccines has been shown in many cases to increase the immunogenicity of protein antigens and is therefore another preferred embodiment of the invention. Microparticles are made either as co-formulations of antigen with a polymer, a lipid, a carbohydrate or other molecules suitable for making the particles, or the microparticles can be homogeneous particles consisting of only the antigen itself.

Examples of polymer based microparticles are PLGA and PVP based particles (Gupta, R. K. et. al. 1998) where the polymer and the antigen are condensed into a solid particle. Lipid based particles can be made as micelles of the lipid (so-called liposomes) entrapping the antigen within the micelle (Pietrobon, P. J. 1995). Carbohydrate based particles are typically made of a suitable degradable carbohydrate such as starch or chitosan. The carbohydrate and the antigen are mixed and condensed into particles in a process similar to the one used for polymer particles (Kas, H. S. et. al. 1997).

Particles consisting only of the antigen can be made by various spraying and freeze-drying techniques. Especially suited for the purporses of the present invention is the super critical fluid technology that is used to make very uniform particles of controlled size (York, P. 1999 & Shekunov, B. et. al. 1999).

It is expected that the vaccine should be administered 1–6 times per year, such as 1, 2, 3, 4, 5, or 6 times a year to an individual in need thereof. It has previously been shown that the memory immunity induced by the use of the preferred autovaccines according to the invention is not permanent, and therefore the immune system needs to be periodically challenged with the amyloidogenic polypeptide or modified amyloidogenic polypeptides.

Due to genetic variation, different individuals may react with immune responses of varying strength to the same polypeptide. Therefore, the vaccine according to the invention may comprise several different polypeptides in order to increase the immune response, cf. also the discussion above concerning the choice of foreign T-cell epitope introductions. The vaccine may comprise two or more polypeptides, where all of the polypeptides are as defined above.

The vaccine may consequently comprise 3–20 different modified or unmodified polypeptides, such as 3–10 different polypeptides.

Nucleic Acid Vaccination

As an alternative to classic administration of a peptide-based vaccine, the technology of nucleic acid vaccination (also known as "nucleic acid immunisation", "genetic immunisation", and "gene immunisation") offers a number of attractive features.

First, in contrast to the traditional vaccine approach, nucleic acid vaccination does not require resource consuming large-scale production of the immunogenic agent (e.g. in the form of industrial scale fermentation of microorganisms producing modified amyloidogenic polypeptides). Furthermore, there is no need to device purification and refolding schemes for the immunogen. And finally, since nucleic acid vaccination relies on the biochemical apparatus of the vaccinated individual in order to produce the expression product of the nucleic acid introduced, the optimum post-translational processing of the expression product is expected to occur; this is especially important in the case of autovaccination, since, as mentioned above, a significant fraction of the original B-cell epitopes should be preserved in the modified molecule, and since B-cell epitopes in principle can be constituted by parts of any (bio)molecule (e.g. carbohydrate, lipid, protein etc.). Therefore, native glycosylation and lipidation patterns of the immunogen may very well be of importance for the overall immunogenicity and this is best ensured by having the host producing the immunogen.

Hence, a preferred embodiment of the invention comprises effecting presentation of modified amyloidogenic polypeptide to the immune system by introducing nucleic acid(s) encoding the modified amyloidogenic polypeptide into the animal's cells and thereby obtaining in vivo expression by the cells of the nucleic acid(s) introduced.

In this embodiment, the introduced nucleic acid is preferably DNA which can be in the form of naked DNA, DNA formulated with charged or uncharged lipids, DNA formulated in liposomes, DNA included in a viral vector, DNA formulated with a transfection-facilitating protein or polypeptide, DNA formulated with a targeting protein or polypeptide, DNA formulated with Calcium precipitating agents, DNA coupled to an inert carrier molecule, DNA encapsulated in a polymer, e.g. in PLGA (cf. the microencapsulation technology described in WO 98/31398) or in chitin or chitosan, and DNA formulated with an adjuvant. In this context it is noted that practically all considerations pertaining to the use of adjuvants in traditional vaccine formulation apply for the formulation of DNA vaccines. Hence, all disclosures herein which relate to use of adjuvants in the context of polypeptide based vaccines apply mutatis mutandis to their use in nucleic acid vaccination technology.

As for routes of administration and administration schemes of polypeptide based vaccines which have been detailed above, these are also applicable for the nucleic acid vaccines of the invention and all discussions above pertaining to routes of administration and administration schemes for polypeptides apply mutatis mutandis to nucleic acids. To this should be added that nucleic acid vaccines can suitably be administered intraveneously and intraarterially. Furthermore, it is well-known in the art that nucleic acid vaccines can be administered by use of a so-called gene gun, and hence also this and equivalent modes of administration are regarded as part of the present invention. Finally, also the use of a VLN in the administration of nucleic acids has been reported to yield good results, and therefore this particular mode of administration is particularly preferred.

Furthermore, the nucleic acid(s) used as an immunization agent can contain regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitope is produced as a fusion partner to the immunomodulator. Alternatively, two distinct nucleotide fragments can be used, but this is less preferred because of the advantage of ensured co-expression when having both coding regions included in the same molecule.

Accordingly, the invention also relates to a composition for inducing production of antibodies against an amyloidogenic polypeptide, the composition comprising a nucleic acid fragment or a vector of the invention (cf. the discussion of vectors below), and a pharmaceutically and immunologically acceptable vehicle and/or carrier and/or adjuvant as discussed above.

Under normal circumstances, the variant-encoding nucleic acid is introduced in the form of a vector wherein expression is under control of a viral promoter. For more detailed discussions of vectors according to the invention, cf. the discussion below. Also, detailed disclosures relating to the formulation and use of nucleic acid vaccines are available, cf. Donnelly J J et al, 1997, Annu. Rev. Immunol. 15: 617–648 and Donnelly J J et al., 1997, Life Sciences 60: 163–172. Both of these references are incorporated by reference herein.

Live Vaccines

A third alternative for effecting presentation of modified amyloidogenic polypeptide to the immune system is the use of live vaccine technology. In live vaccination, presentation to the immune system is effected by administering, to the animal, a non-pathogenic microorganism which has been transformed with a nucleic acid fragment encoding a modified amyloidogenic polypeptide or with a vector incorporating such a nucleic acid fragment. The non-pathogenic microorganism can be any suitable attenuated bacterial strain (attenuated by means of passaging or by means of removal of pathogenic expression products by recombinant DNA technology), e.g. *Mycobacterium bovis* BCG., non-pathogenic *Streptococcus* spp., *E. coli, Salmonella* spp., *Vibrio cholerae, Shigella*, etc. Reviews dealing with preparation of state-of-the-art live vaccines can e.g. be found in Saliou P, 1995, Rev. Prat. 45: 1492–1496 and Walker PD, 1992, Vaccine 10: 977–990, both incorporated by reference herein. For details about the nucleic acid fragments and vectors used in such live vaccines, cf. the discussion below.

As an alternative to bacterial live vaccines, the nucleic acid fragment of the invention discussed below can be incorporated in a non-virulent viral vaccine vector such as a vaccinia strain or any other suitable pox virus.

Normally, the non-pathogenic microorganism or virus is administered only once to the animal, but in certain cases it may be necessary to administer the microorganism more than once in a lifetime in order to maintain protective immunity. It is even contemplated that immunization schemes as those detailed above for polypeptide vaccination will be useful when using live or virus vaccines.

Alternatively, live or virus vaccination is combined with previous or subsequent polypeptide and/or nucleic acid vaccination. For instance, it is possible to effect primary immunization with a live or virus vaccine followed by subsequent booster immunizations using the polypeptide or nucleic acid approach.

The microorganism or virus can be transformed with nucleic acid(s) containing regions encoding the $1^{st}$, $2^{nd}$ and/or $3^{rd}$ moieties, e.g. in the form of the immunomodulating substances described above such as the cytokines discussed as useful adjuvants. A preferred version of this embodiment encompasses having the coding region for the analogue and the coding region for the immunomodulator in different reading frames or at least under the control of different promoters. Thereby it is avoided that the analogue or epitopes are produced as fusion partners to the immunomodulator. Alternatively, two distinct nucleotide fragments can be used as transforming agents. Of course, having the $1^{st}$ and/or $2^{nd}$ and/or $3^{rd}$ moieties in the same reading frame can provide as an expression product, an analogue of the invention, and such an embodiment is especially preferred according to the present invention.

Use of the Method of the Invention in Disease Treatment

As will be appreciated from the discussions above, the provision of the method of the invention allows for control of diseases characterized by amyloid deposits. In this context, AD is the key target for the inventive method but also other diseases characterized by amyloid deposits are feasible targets. Hence, an important embodiment of the method of the invention for down-regulating amyloid activity comprises treating and/or preventing and/or ameliorating AD or other diseases characterized by amyloid deposition, the method comprising down-regulating amyloid according to the method of the invention to such an extent that the amount of amyloid is significantly decreased.

It is especially preferred that the reduction in amyloid results in an inversion of the balance between amyloid formation and amyloid degradation/removal, i.e. that the rate of amyloid degradation/removal is brought to exceed the rate of amyloid formation. By carefully controlling the number and immunological impact of immunizations of the individual in need thereof it will be possible to obtain a balance over time which results in a net reduction of amyloid deposits without having excessive adverse effects.

Alternatively, if in an individual the method of the invention cannot remove or reduce existing amyloid deposits, the method of the invention can be used to obtain a clinically significant reduction in the formation of new amyloid, thereby significantly prolonging the time where the disease condition is non-debilitating. It should be possible to monitor the rate of amyloid depositing by either measuring the serum concentration of amyloid (which is believed to be in equilibrium with the deposited material), or by using positron-emission tomography (PET) scanning, cf. Small G W, et al., 1996, Ann N Y Acad Sci 802: 70–78.

Other diseases and conditions where the present means and methods may be used in treatment or amelioration in an analogous way have been mentioned above in the "Background of the invention" (systemic amyloidosis, maturity onset diabetes, Parkinson's disease, Huntington's disease, fronto-temporal dementia and the prion-related transmissible spongiform encephalopathies) or are listed below in the section headed "other amyloidic diseases and proteins associated therewith".

Peptides, Polypeptides, and Compositions of the Invention

As will be apparent from the above, the present invention is based on the concept of immunising individuals against the amyloidogenic antigen in order to obtain a reduced amount of pathology-related amyloid deposits. The preferred way of obtaining such an immunization is to use modified versions of amyloidogenic polypeptide, thereby providing molecules which have not previously been disclosed in the art.

It is believed that the modified molecules discussed herein are inventive in their own right, and therefore an important part of the invention pertains to an analogue which is derived from an animal amyloidogenic polypeptide wherein is introduced a modification which has as a result that immunization of the animal with the analogue induces production of antibodies reacting specifically with the unmodified amyloidogenic polypeptide. Preferably, the nature of the modification conforms with the types of modifications described above when discussing various embodiments of the method of the invention when using modified amyloidogenic polypeptide. Hence, any disclosure presented herein pertaining to modified amyloidogenic molecules are relevant for the purpose of describing the amyloidogenic analogues of the invention, and any such disclosures apply mutatis mutandis to the description of these analogues.

It should be noted that preferred modified amyloidogenic molecules comprises modifications which results in a polypeptide having a sequence identity of at least 70% with an amyloidogenic protein or with a subsequence thereof of at least 10 amino acids in length. Higher sequence identities are preferred, e.g. at least 75% or even at least 80, 85, 90 or 95%. The sequence identity for proteins and nucleic acids can be calculated as $(N_{ref}-N_{dif})\cdot 100/N_{ref}$, wherein $N_{dif}$ is the total number of non-identical residues in the two sequences when aligned and $N_{ref}$ is the number of residues in one of the sequences. Hence, the DNA sequence AGTCAGTC (SEQ ID NO: 17) will have a sequence identity of 75% with the sequence AATCAATC (SEQ ID NO: 18) ($N_{dif}=2$ and $N_{ref}=8$).

The invention also pertains to compositions useful in exercising the method of the invention. Hence, the invention also relates to an immunogenic composition comprising an immunogenically effective amount of an amyloidogenic polypeptide which is a self-protein in an animal, said amyloidogenic polypeptide being formulated together with an immunologically acceptable adjuvant so as to break the animal's autotolerance towards the amyloidogenic polypeptide, the composition further comprising a pharmaceutically and immunologically acceptable diluent and/or vehicle and/or carrier and/or excipient. In other words, this part of the invention pertains to the formulations of naturally occurring amyloidogenic polypeptides which have been described in connection with embodiments of the method of the invention.

The invention also relates to an immunogenic composition comprising an immunologically effective amount of an analogue defined above, said composition further comprising a pharmaceutically and immunologically acceptable diluent and/or vehicle and/or carrier and/or excipient and optionally an adjuvant. In other words, this part of the invention concerns formulations of modified amyloidogenic polypeptide, essentially as described above. The choice of adjuvants, carriers, and vehicles is accordingly in line with what has been discussed above when referring to formulation of modified and unmodified amyloidogenic polypeptide for use in the inventive method for the down-regulation of amyloid.

The polypeptides are prepared according to methods well-known in the art. Longer polypeptides are normally prepared by means of recombinant gene technology including introduction of a nucleic acid sequence encoding the analogue into a suitable vector, transformation of a suitable host cell with the vector, expression by the host cell of the nucleic acid sequence, recovery of the expression product from the host cells or their culture supernatant, and subsequent purification and optional further modification, e.g. refolding or derivatization.

Shorter peptides are preferably prepared by means of the well-known techniques of solid- or liquid-phase peptide synthesis. However, recent advances in this technology has rendered possible the production of full-length polypeptides and proteins by these means, and therefore it is also within the scope of the present invention to prepare the long constructs by synthetic means.

Nucleic Acid Fragments and Vectors of the Invention

It will be appreciated from the above disclosure that modified amyloidogenic polypeptides can be prepared by means of recombinant gene technology but also by means of chemical synthesis or semisynthesis; the latter two options are especially relevant when the modification consists in coupling to protein carriers (such as KLH, diphtheria toxoid, tetanus toxoid, and BSA) and non-proteinaceous molecules such as carbohydrate polymers and of course also when the modification comprises addition of side chains or side groups to an amyloidogenic polypeptide-derived peptide chain.

For the purpose of recombinant gene technology, and of course also for the purpose of nucleic acid immunization, nucleic acid fragments encoding modified amyloidogenic polypeptide are important chemical products. Hence, an important part of the invention pertains to a nucleic acid fragment which encodes an analogue of an amyloidogenic polypeptide, i.e. an amyloidogenic polypeptide-derived polypeptide which either comprises the natural sequence to which has been added or inserted a fusion partner or, preferably an amyloidogenic polypeptide-derived polypeptide wherein has been introduced a foreign T-cell epitope by means of insertion and/or addition, preferably by means of substitution and/or deletion. The nucleic acid fragments of the invention are either DNA or RNA fragments.

The nucleic acid fragments of the invention will normally be inserted in suitable vectors to form cloning or expression vectors carrying the nucleic acid fragments of the invention; such novel vectors are also part of the invention. Details concerning the construction of these vectors of the invention will be discussed in context of transformed cells and microorganisms below. The vectors can, depending on purpose and type of application, be in the form of plasmids, phages, cosmids, mini-chromosomes, or virus, but also naked DNA which is only expressed transiently in certain cells is an important vector. Preferred cloning and expression vectors of the invention are capable of autonomous replication, thereby enabling high copy-numbers for the purposes of high-level expression or high-level replication for subsequent cloning.

The general outline of a vector of the invention comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma) of or integration into the membrane of the polypeptide fragment, the nucleic acid fragment of the invention, and optionally a nucleic acid sequence encoding a terminator. When operating with expression vectors in producer strains or cell lines it is for the purposes of genetic stability of the transformed cell preferred that the vector when introduced into a host cell is integrated in the host cell genome. In contrast, when working with vectors to be used for effecting in vivo expression in an animal (i.e. when using the vector in DNA vaccination) it is for security reasons preferred that the vector is incapable of being integrated in the host cell genome; typically, naked DNA or non-integrating viral vectors are used, the choices of which are well-known to the person skilled in the art.

The vectors of the invention are used to transform host cells to produce the modified amyloidogenic polypeptide of the invention. Such transformed cells, which are also part of the invention, can be cultured cells or cell lines used for propagation of the nucleic acid fragments and vectors of the invention, or used for recombinant production of the modified amyloidogenic polypeptides of the invention. Alternatively, the transformed cells can be suitable live vaccine strains wherein the nucleic acid fragment (one single or multiple copies) have been inserted so as to effect secretion or integration into the bacterial membrane or cell-wall of the modified amyloidogenic polypeptide.

Preferred transformed cells of the invention are microorganisms such as bacteria (such as the species *Escherichia* [e.g. *E.coli], Bacillus* [e.g. *Bacillus subtilis], Salmonella,* or *Mycobacterium* [preferably non-pathogenic, e.g. *M. bovis* BCG]), yeasts (such as *Saccharomyces cerevisiae*), and protozoans. Alternatively, the transformed cells are derived from a multicellular organism such as a fungus, an insect cell, a plant cell, or a mammalian cell. Most preferred are cells derived from a human being, cf. the discussion of cell lines and vectors below. Recent results have shown great promise in the use of a commercially available *Drosophila melanogaster* cell line (the Schneider 2 ($S_2$) cell line and vector system available from Invitrogen) for the recombinant production of polypeptides in applicants' lab, and therefore this expression system is particularly preferred.

For the purposes of cloning and/or optimized expression it is preferred that the transformed cell is capable of replicating the nucleic acid fragment of the invention. Cells expressing the nucleic fragment are preferred useful embodiments of the invention; they can be used for small-scale or large-scale preparation of the modified amyloidogenic polypeptide or, in the case of non-pathogenic bacteria, as vaccine constituents in a live vaccine.

When producing the modified molecules of the invention by means of transformed cells, it is convenient, although far from essential, that the expression product is either exported out into the culture medium or carried on the surface of the transformed cell.

When an effective producer cell has been identified it is preferred, on the basis thereof, to establish a stable cell line which carries the vector of the invention and which expresses the nucleic acid fragment encoding the modified amyloidogenic polypeptide. Preferably, this stable cell line secretes or carries the analogue of the invention, thereby facilitating purification thereof.

In general, plasmid vectors containing replicon and control sequences which are derived from species compatible with the host cell are used in connection with the hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the prokaryotic microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EP-A-0 036 776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

In addition to prokaryotes, eukaryotic microbes, such as yeast cultures may also be used, and here the promoter should be capable of driving expression. *Saccharomyces cerevisiase*, or common baker's yeast is the most commonly used among eukaryotic microorganisms, although a number of other strains are commonly available. For expression in *Saccharomyces,* the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7 293, *Spodoptera frugiperda* (SF) cells (commercially available as complete expression systems from i.a. Protein Sciences, 1000 Research Parkway, Meriden, Conn. 06450, U.S.A. and from Invitrogen), and MDCK cell lines. In the present invention, an especially preferred cell line is $S_2$ available from Invitrogen, PO Box 2312, 9704 CH Groningen, The Netherlands.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) or may be provided by the host cell chromosomal replication mechanism. If the vector is integrated into the host cell chromosome, the latter is often sufficient.

Identification of Useful Analogues

It will be clear to the skilled person that not all possible variants or modifications of naturally occurring amyloidogenic polypeptides will have the ability to elicit antibodies in an animal which are cross-reactive with the natural form. It is, however, not difficult to set up an effective standard screen for modified amyloidogenic molecules which fulfill the minimum requirements for immunological reactivity discussed herein. Hence, another part of the invention concerns a method for the identification of a modified amyloidogenic polypeptide which is capable of inducing antibodies against unmodified amyloidogenic polypeptide in an animal species where the unmodified amyloidogenic polypeptide is a (non-immunogenic) self-protein, the method comprising preparing, by means of peptide synthesis or genetic engineering techniques, a set of mutually distinct modified amyloidogenic polypeptides wherein amino acids have been added to, inserted in, deleted from, or substituted into the amino acid sequence of an amyloidogenic polypeptide of the animal species thereby giving rise to amino acid sequences in the set which comprise T-cell epitopes which are foreign to the animal species, or preparing a set of nucleic acid fragments encoding the set of mutually distinct modified amyloidogenic polypeptides, testing members of the set of modified amyloidogenic polypeptides or nucleic acid fragments for their ability to induce production of antibodies by the animal species against the unmodified amyloidogenic polypeptide, and identifying and optionally isolating the member(s) of the set of modified amyloidogenic polypeptides which significantly induces antibody production against unmodified amyloidogenic polypeptide in the species or identifying and optionally isolating the polypeptide expression products encoded by members of the set of nucleic acid fragments which significantly induces antibody production against unmodified amyloidogenic polypeptide in the animal species.

In this context, the "set of mutually distinct modified amyloidogenic polypeptides" is a collection of non-identical modified amyloidogenic polypeptides which have e.g. been selected on the basis of the criteria discussed above (e.g. in combination with studies of circular dichroism, NMR spectra, and/or X-ray diffraction patterns). The set may consist of only a few members but it is contemplated that the set may contain several hundred members.

The test of members of the set can ultimately be performed in vivo, but a number of in vitro tests can be applied which narrow down the number of modified molecules which will serve the purpose of the invention.

Since the goal of introducing the foreign T-cell epitopes is to support the B-cell response by T-cell help, a prerequisite is that T-cell proliferation is induced by the modified amyloidogenic polypeptide. T-cell proliferation can be tested by standardized proliferation assays in vitro. In short, a sample enriched for T-cells is obtained from a subject and subsequently kept in culture. The cultured T-cells are contacted with APCs of the subject which have previously taken up the modified molecule and processed it to present its T-cell epitopes. The proliferation of T-cells is monitored and compared to a suitable control (e.g. T-cells in culture contacted with APCs which have processed intact, native amyloidogenic polypeptide). Alternatively, proliferation can be measured by determining the concentration of relevant cytokines released by the T-cells in response to their recognition of foreign T-cells.

Having rendered highly probable that at least one modified amyloidogenic polypeptide of either type of set is capable of inducing antibody production against amyloidogenic polypeptide, it is possible to prepare an immunogenic composition comprising at least one modified amyloid polypeptide which is capable of inducing antibodies against unmodified amyloidogenic polypeptide in an animal species where the unmodified amyloidogenic polypeptide is a self-protein, the method comprising admixing the member(s) of the set which significantly induces production of antibodies in the animal species which are reactive with the amyloidogenic polypeptide with a pharmaceutically and immunologically acceptable carrier and/or vehicle and/or diluent and/or excipient, optionally in combination with at least one pharmaceutically and immunologically acceptable adjuvant.

The above aspects of the invention pertaining to test of polypeptide sets are conveniently carried out by initially preparing a number of mutually distinct nucleic acid sequences or vectors of the invention, inserting these into appropriate expression vectors, transforming suitable host cells (or host animals) with the vectors, and effecting expression of the nucleic acid sequences of the invention. These steps can be followed by isolation of the expression products. It is preferred that the nucleic acid sequences and/or vectors are prepared by methods comprising exercise of a molecular amplification technique such as PCR or by means of nucleic acid synthesis.

Specific Amyloidogenic Targets

In addition to the proteins most often associated with Alzheimer's, APP, ApoE4 and Tau, there is long list of other proteins that have somehow been linked to AD, either by their direct presence in plaques or tangles of AD brains or by their apparent genetic association with increased risk of developing AD. Most, if not all, of these antigens are together with the above-discussed Aβ, APP, presenilin and ApoE4, putative target proteins in the present invention.

Alpha1-antichymotrypsin (ACT) is a major component of SPs and is suggested to play an important role in the pathogenesis of the lesions in AD and cerebrovascular amyloidosis (CA) (Acta neuropathol, 1998, 96: 628–36). It interacts with Aβ in vitro and stimulates both formation and disruption of Aβ-42 fibrils (JBC, 1998, 273: 28360–4).

Alpha2-inacroglobulin was found by immunostaining in plaque cores in AD brains. A transmembrane fragment from the betasubunit was found in plaque cores, while the soluble alpha fragment was found extracellularly in plaques. Acta neuropathol, 1998, 96: 628–36 and Brain Res., 1997, 777: 223–227.

ABAD (Aβ-peptide binding alcohol dehydrogenase) binds with Aβ inside the cell. It is a neuronal enzyme present in normal cells but overexpressed in neurons affected by AD. Aβ is more toxic to cells that overexpress ABAD. ABAD is linked to the X-chromosome. Yan, 1997, Nature 389.

APLP1 and -2 (amyloid precursor like protein 1 and -2): Both proteins belong to the APP homologue super-family proteins, but lack the Aβ peptide region. Nevertheless, there is a significant staining of APLP in neuritic plaques. Acta Neuropathol, 1997, 94: 519–524.

AMY117 is a newly discovered protein in plaque-like lesions in the brains of people with AD which seems abundant, widespread, and "highly specific" for the disease. It is suspected that the protein, AMY117, may play a crucial role in the development and progression AD by forming these plaques. Interestingly, AMY117 containing plaques do not co-localise with those containing Aβ, thus defining a new characteristic manifestation of AD in addition to the well known Aβ containing plaques and Tau containing tangles. AMY117-positive plaques were found to be abundant in the brains of sporadic cases of AD and in brains from people with Down's syndrome, but "rare or absent" in brains of controls and of other neurodegenerative diseases (Am J Pathol 1997; 151: 69,80).

Bax: Monoclonal antibodies has detected Bax as a component of senile plaques in AD brains. Is also overexpressed in dystrophic neurites. Acta Neuropathol. 1998, 95: 407–412.

Bc1–2 has an unclear role. Overexpressed in glial cells surrounding plaques. Acta Neuropathol. 1998, 95: 407–412.

Bleomycin hydrolase is perhaps a beta-secretase. Anti bleomycin hydrolase immunoreactivity has been found in SP in AD (Brain Res. 1999, 830: 200–202). A certain bleomycin hydrolase genotype has been associated with increased risk of developing AD in some cases, while in others no correlation has been found (Ann Neurol, 1998, 44: 808–811 and Ann Neurol, 1999, 46: 136–137).

BRI/ABRI: ABRI is a 4 kD fragment of a putative transmembrane protein, encoded by the BRI gene on chromosome 13, found in amyloid plaques of people with familial British dementia (FBD). These patients have a mutation in the stop codon of the BRI gene that creates a longer open reading frame. Release of the 34 carboxy terminal amino acids of the altered protein generates the ABRI amyloid subunit. Antibodies against ABRI recognise both parenchymal and vascular lesions in the brain of FBD patients. The ABri peptide is deposited as amyloid fibrils and the resulting plaques are thought to lead to the neuronal dysfunction and dementia that characterizes FBD (Vidal, R et. al., 1999, Nature 399).

Chromogranin A has been detected in some diffuse amyloid deposits and in dystrophic neurites surrounding these (Brain Res, 1991, 539: 143–50).

Clusterin/apoJ: This is a gene frequently isolated by differential screening in laboratories from different areas of molecular biology, since it is overexpressed in numerous cases of degenerative diseases such as AD and scrapie (Biochem J 1997 Nov. 15; 328(1):45–50 Michel D, Chatelain G, North S, Brun G).

CRF (corticotropin releasing factor) binding protein binds the 41 aa CRF peptide that is an important regulatory factor in stress responses in the brain. As most CRF is bound by CRF binding protein, removing CRF binding protein (by immunotherapy) could lead to increased level of free CRF, which is believed to have a positive effect against AD. Behan, 1997, J. Neurochemistry, 68: 2053–2060.

EDTF (endothelial-derived toxic factor): A protein produced by microvessels from AD patients. Is specifically toxic to neuronal cells. WO 99/24468.

Heparan sulfate proteoglycans have been shown to co-localise with Aβ in SP's. Rat studies indicate that heparan sulfate glycosaminoglycan is required for amyloid fibre formation (Neuron, 1994, 12: 219–234 and Acta neuropathol, 1998, 96: 628–36).

Human collapsin response mediator protein-2 is 65 kDa protein recognised in neurofibrillary tangles by a monoclonal antibody. Incorporation into tangles may deplete soluble protein and lead to abnormal neuritic outgrowth, thus accelerating neuronal degeneration. JBC, 1998, 273: 9761–8.

Huntingtin (Huntington's disease protein): In HD, the Huntingtin protein is N-terminally expanded with polyglutamine. This form of Huntingtin is also found in NFT's in AD brains and in Pick's disease (Exp. Neurol, 1998, 150: 213–222).

ICAM-I is accumulated in SP's. Acta neuropathol, 1998, 96: 628–36 and Am. J Pathol. 1994, 144: 104–16.

IL-6 is associated with neurofibrillar changes and is found in the centre of plaques. Has been proposes to be a triggering event in AD. Is strongly amplified in astrocytes by the active peptide 25–35 of Aβ. Brain Res., 1997, 777: 223–227 and Behav Brain Res, 1996, 78: 37–41.

Lysosome-associated antigen CD68 is recognised by antibody KP-1 in NFT's and SP's. Thus, lysosomes may play a role in the formation of tangles and plaques. Dement Geriatr Cogn Disord, 1998, 9: 13–19.

P21 ras is involved as a primary step in the elevation of growth factors and mitogens seen at early stages of AD development. Neuroscience, 1999, 91: 1–5.

PLC-delta 1 (phospholipase C isoenzyme delta 1) is abnormally accumulated in NFT's and neurites surrounding plaque cores. Is intracellular. Alzheimer Dis Assoc Disord, 1995, 9: 15–22.

Serum amyloid P component (SAP) is a normal plasma constituent that is present in all types of amyloid deposits, including that of AD (JBC, 1995, 270: 26041–4). It is observed in both SP's and NFT's. In some studies it was shown to promote Aβ aggregation and to prevent proteolysis of fibrils (Biochem Biophys Res commun, 1995, 211: 349v-53 and PNAS, 1995, 92: 4299–4303) while another study indicates that SAP inhibit Aβ fibril formation (JBC, 1995, 270: 26041–4).

Synaptophysin has been detected in some diffuse amyloid deposits and in dystrophic neurites surrounding these. (Brain Res, 1991, 539: 143–50).

Synuclein (alpha-synuclein or NACP): The non-A beta component of AD amyloid (NAC) was identified biochemically as the second major component in the amyloid purified from brain tissue of AD patients. NAC, derived from its 140 amino acid long precursor, NACP, is at least 35 amino acids long (NAC35) although its amino terminus is not definitely determined. An NAC monoclonal antibody immunostains SP's in AD brains, but does not react with NACP (Biochemistry 34 (32): 10139–10145 (Aug. 15, 1995) Iwai A, Yoshimoto M, Masliah E, Saitoh T). NAC self-oligomers in the presence of Aβ. New evidence points to a potential role for this molecule in synaptic damage and neurotoxicity via amyloid-like fibril formation and mitochondrial dysfunction. Brain Pathol 1999 October; 9(4):707–20. FEBS Lett, 1998, 421:73–76. A part of NACP has high homology to the C-terminal amyloid fragment of APP and to a region of scrapie prion protein (PrPSc). Synuclein is a major causative factor of Parkinson's (Chem Biol, 1995, 2: 163–9).

TGF-b1 (transforming growth factor b1): Overexpression of TGF-b1 with mutant APP in TG mice accelerates deposition of Aβ. Thus, TGF-b1 is believed to be involved in initiating or promoting amyloid plaque formation (Wyss-Coray, 1997, Nature 389).

Other Amyloidic Diseases and Proteins Associated Therewith

In addition to the above mentioned proteins that are potentially involved in AD and AD like diseases (Huntington's, Parkinson's, FBD and other forms of dementia), there are a relatively large number of diseases other than AD where amyloid formation is involved in triggering the disease or in causing the symptoms of the disease. Although the proteins involved in these diseases vary in nature they share the same features which define amyloid, cf. above. The following table lists a number of these amyloidic disorders and the proteins causing them.

Diversity of amyloid fibril proteins

| Clinical Syndrome | Fibril subunit | Precursor structure |
|---|---|---|
| Cerebral amyloid angiopathy (CAA) | Aβ | All β |
| Monoclonal protein systemic (AL) amyloidosis | Full length or fragments of V domain of IG light chain | All β |
| Reactive systemic (AA) amyloidosis | 76-residue N-terminal fragment of amyloid A protein | α/β |
| Familial amyloidotic polyneuropathy | Full-length or fragments of transthyretin variants | All β |
| Hereditary ApoAl amyloidosis | N-terminal fragments (~90 residues) of ApoAl variants | (α/β) |
| Hereditary lysozyme amyloidosis | Full-length lysozyme variants | α + β |
| Type II diabetes mellitus | 37-residue fragment of islet-amyloid polypeptide | Unknown |
| Insulin-related amyloid | Full-length wild-type insulin | α + β |
| Transmissible spongioform encephalopathis | Full-length or fragments of prion protein | α + β |
| Medullary carcinoma of the thyroid | Fragments of calcitonin | Unknown |
| Senile systemic amyloidosis | Full-length or fragments of transthyretin | All β |
| Hemodialysis-related amyloidosis | Full-length, wild-type β-2 microglobulin | All β |
| Isolated atrial amyloidosis | Atrial natriuretic factor | Unknown |
| Hereditary cerebral amyloid angiopathy | 110-residue fragment of variant cystatin | α + β |
| Finnish hereditary amyloidosis | 71-residue fragment of gelsolin variants | α/β |
| Hereditary fibrinogen a-chain amyloidosis | Fragments of fibrinogen a-chain variants | Unknown |

These proteins are, like the proteins involved in AD, all potential targets for the immunization strategy suggested herein.

It is contemplated that most methods for immunizing against amyloidogenic polypeptides should be restricted to immunization giving rise to antibodies cross-reactive with the native amyloidogenic polypeptide. Nevertheless, in some cases it will be of interest to induce cellular immunity in the form of CTL responses against cells which present MHC Class I epitopes from the amyloidogenic polypeptides—this can be expedient in those cases wherein reduction in the number of cells producing the amyloidogenic polypeptides does not constitute a serious adverse effect. In such cases where CTL responses are desired it is preferred to utilise the teachings of Applicant's PCT/DK99/00525 (corresponding to U.S. Ser. No. 09/413,186). The disclosures of these two documents are hereby incorporated by reference herein.

In the following non-limiting example, focus has been put on the development of a Aβ based autovaccine against AD. However, the principles set forth herein apply equally to any amyloid protein.

EXAMPLE 1

The Auto Vaccination Approach for Immunizing Against AD

The fact that Aβ protein knock out mice does not show any abnormalities or adverse side effects, suggest that removal or lowering the amounts of Aβ will be safe, Zheng H. (1996).

Published experiments where transgenic animals are immunized against the transgenic human Aβ protein suggest that if it was possible to break the self tolerance, down-regulation of Aβ could be obtained by auto-reactive antibodies. These experiments further suggest that such down regulation of Aβ potentially would both prevent the formation of plaques, and even clear already formed Aβ plaques from the brain, cf. Schenk et al. (1999). But, traditionally it is not possible to raise antibodies against self-proteins.

The published data does thus not provide the means for breaking true self-tolerance towards true self-proteins. Nor does the data provide information on how to ensure that the immune reaction is directed solely or predominantly towards the Aβ deposits, and not towards the cell membrane bound Aβ precursor protein (APP), if this is deemed necessary. An immune response generated using the existing technology would presumably generate an immune response towards self-proteins in an unregulated way so unwanted and excessive auto-reactivity towards parts the Aβ protein may be generated. Hence, using existing immunization strategies will most likely be unable to generate strong immune responses towards self-proteins and will furthermore be unsafe due to potential strong cross-reactivity towards membrane bound APP which is present on a large number of cells in the CNS.

The present invention provides the means of effectively generating a strong regulated immune response towards true self-proteins which potentially could form plaques and cause serious disease in the CNS or in other compartments of the body. A safe and efficacious human Aβ protein therapeutic vaccine will be developed by using this technology for the treatment of AD.

In light of this, it is possible to anticipate that AD, a disease predicted to cripple the health care system in the next century, could be cured, or such vaccines described could at least constitute an effective therapeutical approach for treatment of the symptoms and progression of this disease.

This technique represents a entirely new immunological approach to blocking amyloid deposition in AD and other neurologic diseases as well.

In the following table, 35 contemplated constructs are indicated. All positions given in the table are relative to the starting Methionine of APP (first amino acid in SEQ ID NO: 2) and include both the starting and ending amino acid, e.g. the 672–714 fragment includes both amino acid 672 and 714. The starting and ending positions for P2 and P30 indicate that the epitope substitutes a part of the APP fragment at the positions indicated (both positions included in the substitution)—in most constructs, the introduced epitopes substitutes a fragment of the length of the epitope. The asterisks in the table have the following meaning:

APP AutoVac constructions

| Var. No. | Start of APP segment relative to aa 1 of APP | End of APP segment relative to aa 1 of APP | Position of P2 epitope relative to aa 1 of APP | Position of P30 epitope relative to aa 1 of APP | Molecule length |
|---|---|---|---|---|---|
| 1 | 630 | 770 | 656–670 | 635–655 | 141 |
| 2 | 630 | 714 | 656–670 | 635–655 | 85 |
| 3 | 672 | 770 | 735–749 | 714–728 | 99 |
| 4 | 672 | 770 | | 714–728 | 99 |
| 5 | 672 | 770 | 714–728 | | 99 |
| 6 | 672 | 770 | 723* | 723* | 135 |
| 7 | 672 | 770 | | 723* | 120 |
| 8 | 672 | 770 | 723* | | 114 |
| 9 | 672 | 714 | | 672* | 64 |
| 10 | 672 | 714 | | 714* | 64 |
| 11 | 672 | 714 | 672* | | 58 |
| 12 | 672 | 714 | 714* | | 58 |
| 13 | 672 | 714 | 714* | 672* | 79 |
| 14 | 672 | 714 | 680–694 | | 43 |
| 14 | 672 | 714 | 685–799 | | 43 |
| 16 | 672 | 714 | 690–704 | | 43 |
| 17 | 672 | 714 | 695–709 | | 43 |
| 18 | 672 | 714 | | 675–695 | 43 |
| 19 | 672 | 714 | | 680–700 | 43 |
| 20 | 672 | 714 | | 685–705 | 43 |

-continued

APP AutoVac constructions

| Var. No. | Start of APP segment relative to aa 1 of APP | End of APP segment relative to aa 1 of APP | Position of P2 epitope relative to aa 1 of APP | Position of P30 epitope relative to aa 1 of APP | Molecule length |
|---|---|---|---|---|---|
| 21 | 672 | 714 | | 690–710 | 43 |
| 22 | 672 | 714 | 680* | 680* | 79 |
| 23 | 672 | 714 | 690* | 690* | 79 |
| 24 | 672 | 714 | 700* | 700* | 79 |
| 25 | 672 | 714 | 710* | 710* | 79 |
| 26 | 672 | 714 | | 680* | 64 |
| 27 | 672 | 714 | | 690* | 64 |
| 28 | 672 | 714 | | 700* | 64 |
| 29 | 672 | 714 | | 710* | 64 |
| 30 | 672 | 714 | 680* | | 58 |
| 31 | 672 | 714 | 690* | | 58 |
| 32 | 672 | 714 | 700* | | 58 |
| 33 | 672 | 714 | 710* | | 58 |
| 34 | 672 | 714 | After rep. 1** | After rep. 2** | 165 |
| 35 | 672 | 714 | 34 x 3* | 34 x 3*** | 165 |

*Only one position for P2 and P30 indicates that the epitope has been inserted into the APP derivative at the position indicated (the epitope begins at the amino acid C-terminally adjacent to the given position).
**Construction 34 contains three identical APP fragments separated by P30 and P2, respectively.
***Construction 35 contains nine identical APP fragments separated by alternating P30 and P2 epitopes.

The part of APP against which it most interesting to generate a response is the 43 amino acid Aβ core peptide (Aβ-43, corresponding to SEQ ID NO: 2, residues 672–714) that is the main constituent of amyloid plaques in AD brains. This APP fragment is part of all constructions listed above.

Variants 1 and 2 comprise a portion of APP upstream of Aβ-43 where the model epitopes P2 and P30 have been placed. Variants 1 and 3–8 all comprise the C-100 fragment which has been shown to be neurotoxic—the C-100 fragment corresponds to amino acid residues 714–770 of SEQ ID NO: 2. In variants 3–5 the epitopes substitutes a part of the C-100 fragment while the in variants 6–8 have been inserted into C-100.

Variants 9–35 contain only the core Aβ-43 protein. In variants 9–13, P2 and P30 are fused to either end of Aβ-43; in 14–21 P2 and P30 substitutes part of Aβ-43; in 22–33 P2 and P30 are inserted into Aβ-43; 34 contains three identical Aβ-43 fragments spaced by P30 and P2, respectively; 35 contains 9 Aβ-43 repeats spaced by alternating P2 and P30 epitopes.

See FIG. 1 and the table above for details.

One further type of construct is especially preferred. Since one goal of the present invention is to avoid destruction of the cells producing APP whereas removal of Aβ is desired, it seems feasible to prepare autovaccine constructs comprising only parts of Aβ which are not exposed to the extracellular phase when present in APP. Thus, such constructs would need to contain at least one B-cell epitope derived from the amino acid fragment defined by amino acids 700–714 in SEQ ID NO: 2.

Since such a short polypeptide fragment is predicted to be only weakly immunogenic it is preferred that such an autovaccine construct consists of several copies of the B-cell epitope, e.g. in the form of a construct having the structure shown in Formula I in the detailed disclosure of the present invention, cf. above. In that version of Formula I, the terms amyloide$_{e1}$-amyloid$_{ex}$ are x B-cell epitope containing amino acid sequences derived from amino acids 700–714 of SEQ ID NO: 2. A preferred alternative is the above-detailed possibility of coupling the amyloidogenic (poly)peptide and the selected foreign T-helper epitope to via an amide bond to a polysaccharide carrier molecule—in this way multiple presentations of the “weak” epitope constituted by amino acids 700–714 of SEQ ID NO: 2 become possible, and it also becomes possible to select an optimum ratio between B-cell and T-cell epitopes.

EXAMPLE 2

Immunisation of Transgenic Mice with Aβ and Modified Proteins According to the Invention Construction of the hAB43+-34 encoding DNA. The hAB43+-34 gene was constructed in several steps. First a PCR fragment was generated with primers ME#801 (SEQ ID NO: 10) and ME#802 (SEQ ID NO: 11) using primer ME#800 (SEQ ID NO: 9) as template. ME#800 encodes the human abeta-43 fragment with *E. coli* optimised codons. ME#801 and 802 adds appropriate restriction sites to the fragment.

The PCR fragment was purified, digested with NcoI and HindIII, purified again and cloned into NcoI-HindIII digested and purified pET28b+ *E. coli* expression vector. The resulting plasmid encoding wildtype human Aβ-43 is named pAB1.

In the next step the T-helper epitope, P2, is added to the C-terminus of the molecule. Primer ME#806 (SEQ ID NO: 12) contains the sequence encoding the P2 epitope, thus generating a fusion of P2 and Abeta-43 by the PCR reaction.

The cloning was performed by making a PCR fragment with primers ME#178 (SEQ ID NO: 8) and ME#806 using pAR1 as template. The fragment was purified, digested with NcoI and HindIII, purified again and cloned into an NcoI-HindIII digested and purified pET28b+ vector. The resulting plasmid is called pAB2.

In an analogous manner, another plasmid was made harbouring the Aβ-43 encoding sequence with another T helper epitope, P30, added to the N-terminus. This was done by making a PCR fragment with primers ME#105 (SEQ ID NO: 7) and ME#807 (SEQ ID NO: 13) using pAE1 as template.

The fragment was purified, digested with NcoI and HindIII, purified again and cloned into an NcoI-HindIII digested and purified pET28b+ vector. The resulting plasmid is called pAB3.

In the third step, a second Aβ-43 repeat is added C-terminally to the P2 epitope of plasmid pAB2 by primer ME#809 (SEQ ID NO: 14). ME#809 at the same time creates a BamHI site immediately after the Aβ-43 repeat. A PCR fragment was made with primers ME#178 and ME#809 using pAB2 as template. The fragment was digested with NcoI and HindIII, purified and cloned into NcoI-HindIII digested and purified pET28b+ vector. This plasmid is named pAB4.

Finally, the P30 epitope—Aβ-43 repeat sequence from pAB3 was cloned into pAB4 plasmid. This was done by making a PCR fragment with primers ME#811 (SEQ ID NO: 16) and ME#105 using pAB3 as template. The fragment was purified and used as primer in a subsequent PCR with ME#810 (SEQ ID NO: 15) using pAB3 as template. The resulting fragment was purified, digested with BamHI and HindIII and cloned into BamHI-HindIII digested and purified pAB4 plasmid. The resulting plasmid, pAB5, encodes the hAB43+-34 molecule.

All PCR and cloning procedures were done essentially as described by Sambrook, J., Fritsch, E. F. & Maniatis, T. 1989 "Molecular cloning: a laboratory manual". 2nd. Ed. Cold Spring Harbor Laboratory, N.Y.

For all cloning procedures *E. coli* K-12 cells, strain Top-10 F' (Stratagene, USA), were used. The pET28b+ vector was purchased from Novagen, USA. All primers were synthesised at DNA Technology, Denmark.

Expression and purification of hAB43+-34. The hAB43+-34 protein encoded by pAB5 was expressed in BL21-Gold (Novagen) *E. coli* cells as described by the suppliers of the pET28b+ system (Novagen).

The expressed hAB43+-34 protein was purified to more than 85% purity by washing of inclusion bodies followed by cation-exchange chromatography using a BioCad purification workstation (PerSeptive Biosystems, USA) in the presence of 6 M urea. The urea was hereafter removed by stepwise dialysis against a solution containing decreasing amounts of urea. The final buffer was 10 mM Tris, pH 8.5.

Immunisation study. Mice transgenic for human APP (Alzheimer's precursor protein) were used for the study. These mice, called TgRND8+, express a mutated form of APP that results in high concentration of Aβ-40 and Aβ-42 in the mouse brains (Janus, C. et. al.)

The mice (8–10 mice per group) were immunised with either Abeta-42 (SEQ ID NO: 2, residues 673–714, synthesised by means of a standard Fmoc strategy) or the hAB43+-34 variant (construct 34 in the table in Example 1, recombinantly produced) four times at two-week intervals. Doses were either 100 mg for Aβ or 50 mg for hAB43+-34. Mice were bled at day 43 (after three injections) and after day 52 (after four injections) and the sera were used to determine the level of anti-Aβ-42 specific titres using a direct Aβ-42 ELISA.

The following tabel shows the mean relative anti-Abeta-42 titres.

| Immunogen | Day 43 (after 3 immunizations) | Day 52 (after 4 immunizations) |
|---|---|---|
| Aβ-42 | 4000 | 3000 |
| hAB43+-34 | 16000 | 23000 |

As will be clear, the antibody titers obtained when immunizing with the hAB43+-34 Aβ variant are approximately 4 times and 7.5 times higher after 3 and 4 immunizations, respectively, than the titers obtained when using the unaltered wild-type Aβ-42 as an immunogen. This fact is put further in perspective, when considering the fact that the amount of variant used for immunization was only 50% of the amount of wild-type sequence used for immunization.

EXAMPLE 3

Synthesis of an Aβ Peptide Copolymer Vaccine Using Activated poly-hydroxypolymer as the Cross-linking Agent.

Introduction. A traditional conjugate vaccine consists of a (poly)peptide coupled covalently to a carrier protein. The peptide contains the B-cell epitope(s) and the carrier protein provides T-helper epitopes. However, most of the carrier protein will normally be irrelevant as a source for T-helper epitopes, since only a minor part of the total sequence contains the relevant T-helper epitopes. Such epitopes can be defined and synthesized as peptides of e.g. 12–15 amino acids. If these peptides are linked covalently to peptides containing the B-cell epitopes, e.g. via a multivalent activated poly-hydroxypolymer, a vaccine molecule that only contains the relevant parts can be obtained. It is further possible to provide a vaccine conjugate that contains an optimized ratio between B-cell and T-cell epitopes.

Synthesis of the acticated poly-hydroxypolymer. Poly-hydroxypolymers such as dextran, starch, agarose etc. can be activated with 2,2,2-trifluoroethanesulfonyl chloride (tresyl chloride), either by means of a homogenous synthesis (dextran) dissolved in N-methylpyrrolidinone (NMP) or by means of a heterogeneous synthesis (starch, agarose, cross-linked dextran) in e.g. acetone.

225 ml dry N-methyl pyrrolidinone (NMP) is added under dry conditions to freeze dried, water-soluble dextran (4.5 g, 83 mmol, clinical grade, Mw(avg) 78000) in a 500 ml round bottom flask supplied with a magnet for stirring. The flask is placed in a 60° C. oil bath with magnetic stirring. The temperature is raised to 92° C. over a period of 20 min. When the dextran is dissolved the flask is immediately removed from the oil bath and the temperature in the bath is lowered to 40° C. The flask is placed into the oil bath agaom, still with magnetic stirring, and tresyl chloride (2.764 ml, 25 mmol) is added drop-wise. After 15 min, dry pyridine (anhydrous, 2.020 ml, 25 mmol) is added drop-wise. The flask is removed from the oil bath and stirred for 1 hour at room temperature. The product (Tresyl Activated Dextran, TAD) is precipitated in 1200 ml cold ethanol (99.9%). The supernatant is decanted and the precipitate is harvested in 50 ml polypropylene tubes in a centrifuge at 2000 rpm. The precipitate is dissolved in 50 ml 0.5% acetic acid, dialyzed 2 times against 5000 ml 0.5% acetic acid and freeze dried. TAD can be stored as a freeze dried powder at −20° C.

An insoluble poly-hydroxypolymer, such as agarose or croos-linked dextran can be tresyl activated by making a suspension of the poly-hydroxypolymer in e.g. acetone and perform the synthesis as a solid phase synthesis. The activated poly-hydroxypolymer can be harvested by filtration. Suitable methods are reported in e.g. Nilsson K and Mosbach K (1987), Methods in Enzymology 135, p. 67, and in Hermansson GT et al. (1992), in "Immobilized Affinity Ligand Techniques", Academic Press, Inc., p. 87.

Synthesis of the A Beta Peptide Copolymers Vaccines. TAD (10 mg) is dissolved in 100 μl $H_2O$ and 1000 μl carbonate buffer, pH 9.6, containing 5 mg Aβ-42 (SEQ ID NO: 2, residues 673–714), 2.5 mg P2 (SEQ ID NO: 4) and 2.5 mg P30 (SEQ ID NO: 6) is added. The Aβ-42 and the P2 and P30 peptides all contain protected lysine groups: these are in the form of 1-(4,4-Dimethyl-2,6-dioxocyclohex-1-ylidene)ethyl (Dde) protected lysine groups. The peptides are prepared by means of a standard Fmoc strategy, where the conventional Fmoc-Lys(Boc)-OH has been substituted with Fmoc-Lys(Dde)-OH (obtained from Novabiochem , cat. no. 04–12–1121), i.e. the ε-amino group in lysine is protected with Dde instead of Boc.

The pH value is measured and adjusted to 9.6 using 1 M HCl. After 2.5 hours at room temperature, hydrazine from an 80% solution is added to a final hydrazine Concentration of 8% and the solution is incubated for another 30 min. at room temperature and freeze-dried immediately hereafter. The freeze-dried product is dissolved in $H_2O$ and dialysed extensively against $H_2O$ before the final freeze-drying.

The ratio between B-cell epitopes (Aβ) and T-helper epitopes (P2 and P30) in the final product can be varied by using different concentrations of these peptides in the synthesis step. Furthermore, the final product can be tagged with e.g. mannose (so as to target the conjugate to APCs) by adding aminated mannose to the carbonate buffer in the synthesis step.

If an insoluble activated poly-hydroxypolymer is used to combine the peptides containing the B-cell epitope and the T-helper epitopes, the coupling to the polymer can be performed as a solid phase synthesis and the final product is harvested and purified by wash and filtration.

LIST OF REFERENCES

Brookmeyer, R.; Gray, S.; Kawas, C. (1998). Projections of Alzheimer's Disease in the United States and the Public Health Impact of Delaying Disease Onset. American Journal of Public Health, 88(9), 1337–1342.

Buttini, M.; Orth, M.; Bellosta, S.; Akeefe, H.; Pitas, R. E.; Wyss-Coray, T.; Mucke, L.; Mahley, R. W. (1999). Expression of Human Apolipoprotein E3 or E4 in the Brains of Apoe−/− Mice: Isoform-Specific Effects on Neurodegeneration. Journal of Neuroscience, 19, 4867–4880.

Clark, L. N.; Poorkaj, P.; Wszolek, Z.; Geschwind, D. H.; Nasreddine, Z. S.; Miller, B.; Li, D.; Payami, H.; Awert, F.; Markopoulou, K.; Andreadis, A.; D'Souza, I.; Lee, V. M.; Reed, L.; Trojanowski, J. Q.; Zhukareva, V.; Bird, T.; Schellenberg, G.; Wilhelmsen, K. C. (1998). Pathogenic Implications of Mutations in the Tau Gene in Pallido-Ponto-Nigral Degeneration and Related Neurodegenerative Disorders Linked to Chromosome 17. Proceedings of the National Academy of Sciences U.S.A., 95(22), 13103–13107.

Gupta, R. K. et. al. (1998), Dev Biol Stand. 92: 63–78.

Hsiao K. et al. (1998) Transgenic mice expressing Alzheimer amyloid precursor proteins", Exp. Gerontol. 33 (7–8), 883–889

Hutton, M.; Lendon, C. L.; Rizzu, P.; Baker, M.; Froelich, S.; Houlden, H.; Pickering-Brown, S.; Chakraverty, S.; Isaacs, A.; Grover, A.; Hackett, J.; Adamson, J.; Lincoln, S.; Dickson, D.; Davies, P.; Petersen, R. C.; Stevens, M.; de Graaff, E.; Wauters, E.; van Baren, J.; Hillebrand, M.; Joosse, M.; Kwon, J. M.; Nowotny, P.; Che, L. K.; Norton, J.; Morris, J. C.; Reed, L. E.; Trojanowski, J.; Basun, H.; Lannfelt, L.; Neystat, M.; Fahn, S.; Dark, F.; Tannenberg, T.; Dodd, P.; Hayward, N.; Kwok, J. B. J.; Schofield, P. R.; Andreadis, A.; Snowden, J.; Craufurd, D.; Neary, D.; Owen, F.; Oostra, B. A.; Hardy, J.; Goate, A.; van Swieten, J.; Mann, D.; Lynch, T.; Heutink, P. (1998). Association of Missense and 5'-Splice-Site Mutations in Tau with the Inherited Dementia FTDP-17. Nature, 393, 702–705.

Janus, C. et. al. (2000), Nature 408: 979–982.

Kas, H. S. (1997) J Microencapsul 14: 689–711

Leon, J.; Cheng, C. K.; Neumann, P. J. (1998). Alzheimer's Disease Care: Costs and Potential Savings. Health Affairs, 17(6), 206–216.

Lippa C. F. et al. (1998) Ab-42 deposition precedes other changes in PS-1 Alzheimer's disease. Lancet 352, 1117–1118

Luo, J.-J.; Wallace, W.; Riccioni, T.; Ingram, D. K.; Roth, G. S.; Kusiak, J. W. (1999). Death of PC12 Cells and Hippocampal Neurons Induced by Adenoviral-Mediated FAD Human Amyloid Precursor Protein Gene Expression. Journal of Neuroscience Research, 55(5), 629–642.

Naruse, S.; Thinakaran, G.; Luo, J.-J.; Kusiak, J. W.; Tomita, T.; Iwatsubo, T.; Qian, X.; Ginty, D. D.; Price, D. L.; Borchelt, D. R.; Wong, P. C.; Sisodia, S. S. (1998). Effects of PS1 Deficiency on Membrane Protein Trafficking in Neurons. Neuron, 21(5), 1213–1231.

National Institute on Aging Progress Report on Alzheimer's Disease, 1999, NIH Publication No. 99–4664.

Pietrobon, P. J. (1995), Pharm Biotechnol. 6: 347–61Poorkaj, P.; Bird, T. D.; Wijsman, E.; Nemens, E.; Garruto, R. M.; Anderson, L.; Andreadis, A.; Wiederhold, W. C.; Raskind, M.; Schellenberg, G. D. (1998). Tau Is a Candidate Gene for Chromosome 17 Frontotemporal Dementia. Annals of Neurology, 43, 815–825.

Schenk, D.; Barbour, R.; Dunn, W.; Gordon, G.; Grajeda, H.; Guido, T.; Hu, K.; Huang, J.; Johnson-Wood, K.; Khan, K.; Kholodenko, D.; Lee, M.; Liao, Z.; Lieberburg, I.; Motter, R.; Mutter, L.; Soriano, F.; Shopp, G.; Vasquez, N.; Vandevert, C.; Walker, S.; Wogulis, M.; Yednock, T.; Games, D.; Seubert, P. (1999). Immunization with A-beta Attenuates Alzheimer's Disease-Like Pathology in the PDAPP Mouse. Nature, 400(6740), 173–177.

Shekunov, B. et. al. (1999), J. Crystal Growth 198/199: 1345–1351.

Spillantini, M. G.; Murrell, J. R.; Goedert, M.; Farlow, M. R.; Klug, A.; Ghetti, B. (1998). Mutation in the Tau Gene in Familial Multiple System Tauopathy with Presenile Dementia. Proceedings of the National Academy of Sciences U.S.A., 95(13), 7737–7741.

Strittmatter, W. J.; Saunders, A. M.; Schmechel, D.; Pericak-Vance, M.; Enghild, J.; Salvesen, G. S.; Roses, A. D. (1993). Apolipoprotein E: High-Avidity Binding to Aβ and Increased Frequency of Type 4 Allele in Late-Onset Familial Alzheimer Disease. Proceedings of the National Academy of Sciences U.S.A., 90,1977–1981.

Vidal, R.; Frangione, B.; Rostagno, A.; Mead, S.; Revesz, T.; Plant, G.; Ghiso, J. (1999). A Stop-Codon Mutation in the BRI Gene Associated with Familial British Dementia. Nature, 399: 776–781.

Zheng H. (1996) "Mice deficient for the amyloid precursor protein gene. Ann. N Y Acad. Sci., 777, 421–426.

York, P. (1999), PSTT 11: 430–440

The invention claimed is:

1. A method for reducing amyloid plaque burden in a mammal, the method comprising:

administering an immunogenically effective amount of at least one modified Aβ or APP polypeptide, wherein said modified Aβ or APP polypeptide differs from the mammal's autologous Aβ or autologous APP polypeptide in that it comprises at least one isolated foreign T helper epitope inserted into said autologous Aβ or autologous APP polypeptide and wherein said at least one isolated T helper epitope is selected from the group consisting of a Tetanus toxoid epitope, a diphtheria toxoid epitope, an influenza virus hemagglutinin epitope, a *P.falciparum* CS epitope and an artificial MHC-II binding peptide sequence whereby administration to said mammal with said modified Aβ or APP polypeptide induces production of antibodies against the autologous Aβ or autologous APP polypeptide in said mammal.

2. The method according to claim 1, wherein said modified Aβ or APP polypeptide further comprises:

(a) at least one first moiety which is a specific binding partner, selected from the group consisting of a hapten and a carbohydrate, for a receptor on a B-lymphocyte or an antigen presenting cell (APC), which targets the modified Aβ or APP polypeptide to an antigen presenting cell (APC) or a B-lymphocyte, and/or (b) at least one second moiety selected from the group consisting of a cytokine, heat shock protein or hormone, which stimulates the immune system, and/or (c) at least one third moiety selected from the group consisting of a lipid and a polyhydroxypolymer, which optimizes presentation of the modified Aβ or APP polypeptide to the immune system.

3. A method for reducing amyloid plaque burden in a mammal, the method comprising:

administering an immunogenically effective amount of at least one modified Aβ or APP polypeptide, wherein said modified Aβ or APP polypeptide differs from the mammal's autologous Aβ or autologous APP polypeptide in that it comprises at least one isolated foreign T helper epitope inserted into said autologous Aβ or autologous APP polypeptide and wherein said at least one isolated T helper epitope is selected from the group consisting of a Tetanus toxoid epitope, a diphtheria toxoid epitope, an influenza virus hemagglutinin epitope, a *P.falciparum* CS epitope and a pan DR epitope peptide whereby administration to said mammal with said modified Aβ or APP polypeptide induces production of antibodies against the autologous Aβ or autologous APP polypeptide in said mammal.

4. The method according to claim 3, wherein the modification further comprises:

(a) at least one first moiety which is a specific binding partner, selected from the group consisting of a hapten and a carbohydrate, for a receptor on a B-lymphocyte or an antigen presenting cell (APC), which targets the modified Aβ or APP polypeptide to an antigen presenting cell (APC) or a B-lymphocyte, and/or (b) at least one second moiety selected from the group consisting of a cytokine, heat shock protein or hormone, which stimulates the immune system, and/or (c) at least one third moiety selected from the group consisting of a lipid and a polyhydroxypolymer, which optimizes presentation of the modified Aβ or APP polypeptide to the immune system.

5. A method according to 1, wherein the modified Aβ or APP polypeptide is selected from the group consisting of (a) three identical APP fragments consisting of amino acids 672–714 of SEQ ID NO: 2 separated by the at least one isolated foreign T helper epitope, (b) nine identical APP fragments consisting of amino acids 672–714 of SEQ ID NO: 2 separated by the at least one isolated foreign T helper epitope, (c) amino acids 672–714 of SEQ ID NO: 2 having an isolated foreign T helper epitope fused to the N- or C-terminus;

(d) amino acids 672–714 of SEQ ID NO: 2 wherein has been introduced an isolated foreign T helper epitope by means of substitution;

(e) amino acids 672–714 of SEQ ID NO: 2, wherein has been introduced an isolated foreign T-helper epitope by means of insertion, (f) amino acids 672–770 of SEQ ID NO: 2 wherein has been introduced at least one isolated foreign T helper epitope by means of substitution into amino acids 714–770;

(g) amino acids 672–770 of SEQ ID NO: 2 wherein has been introduced at least one isolated foreign T helper epitope by means of insertion into amino acids 714–770; and (h) amino acids 630–770 of SEQ ID NO: 2 wherein has been introduced at least one isolated foreign T helper epitope by means of substitution into amino acids 630–672; and (i) amino acids 630–714 of SEQ ID NO: 2 wherein has been introduced at least one isolated foreign T helper epitope by means of insertion into amino acids 630–672.

6. A method according to 3, wherein the modified Aβ or APP polypeptide is selected from the group consisting of (a) three identical APP fragments consisting of amino acids 672–714 of SEQ ID NO: 2 separated by the at least one isolated foreign T helper epitope, (b) nine identical APP fragments consisting of amino acids 672–714 of SEQ ID NO: 2 separated by the at least one isolated foreign T helper epitope, (c) amino acids 672–714 of SEQ ID NO: 2 having an isolated foreign T helper epitope fused to the N- or C-terminus;

(d) amino acids 672–714 of SEQ ID NO: 2 wherein has been introduced an isolated foreign T helper epitope by means of substitution;

(e) amino acids 672–714 of SEQ ID NO: 2, wherein has been introduced an isolated foreign T-helper epitope by means of insertion, (f) amino acids 672–770 of SEQ ID NO: 2 wherein has been introduced at least one isolated foreign T helper epitope by means of substitution into amino acids 714–770;

(g) amino acids 672–770 of SEQ ID NO: 2 wherein has been introduced at least one isolated foreign T helper epitope by means of insertion into amino acids 714–770; and (h) amino acids 630–770 of SEQ ID NO: 2 wherein has been introduced at least one isolated foreign T helper epitope by means of substitution into amino acids 630–672; and (i) amino acids 630–714 of SEQ ID NO: 2 wherein has been introduced at least one isolated foreign T helper epitope by means of insertion into amino acids 630–672.

7. The method according to claim 1, wherein the foreign T-cell epitope is immunodominant in the mammal.

8. The method according to claim 1, wherein the foreign T-cell epitope is promiscuous.

9. The method according to claim 1, wherein said modified Aβ or APP polypeptide further comprises at least two copies of said polypeptide covalently or non-covalently linked to a carrier molecule.

10. The method according to claim 1, wherein said polypeptide is administered in combination with an adjuvant which facilitates breaking of autotolerance to autoantigens.

11. The method according to claim 1, which includes at least one administration per year.

12. The method according to claim 8, wherein the foreign T-cell epitope is selected from a natural promiscuous T-cell epitope and an artificial MHC-II binding peptide sequence.

13. The method according to claim 1, wherein the tetanus toxoid epitope is selected from the group consisting of SEQ ID NO: 4 and SEQ ID NO: 6.

14. The method according to claim 2, wherein the cytokine is selected from the group consisting of interferon γ, Flt3L, interleukin 1, interleukin 2, interleukin 4, interleukin 6, interleukin 12, interleukin 13, interleukin 15, and granulocyte-macrophage colony stimulating factor.

15. The method according to claim 2, wherein the heat shock protein is selected from the group consisting of HSP70, HSP90, HSC70, GRP94, and calreticulin.

16. The method according to claim 2, wherein the third moiety is a lipid selected from the group consisting of a palmitoyl group, a myristyl group, a farnesyl group, a geranyl-geranyl group, a GPI-anchor, and an N-acyl diglyceride group.

17. The method according to claim 2, wherein the polyhydroxypolymer is a polysaccharide.

18. The method according to claim 11, comprising at least 2 administrations per year.

19. The method according to claim 18, comprising at least 3 administrations per year.

20. The method according to claim 1, wherein the administration is via a parenteral route is selected from the group consisting of the subcutaneous, the intracutaneous, and the intramuscular route.

21. The method according to claim 1, wherein the artificial MHC-II binding peptide sequence is the amino acid sequence of SEQ ID NO. 19.

22. The method according to claim 5, wherein the modified Aβ or APP polypeptide, from the N- to the C-terminus, consists of amino acid residues 672–714 of SEQ ID NO: 2 followed by SEQ ID NO: 4 followed by amino acid residues 672–714 of SEQ ID NO: 2 followed by SEQ ID NO: 6 followed by amino acid residues 672–714 of SEQ ID NO: 2.

23. The method according to claim 5, wherein the modified Aβ or APP polypeptide, from the N- to the C-terminus, consists of amino acid residues 630–634 of SEQ ID NO: 2 followed by SEQ ID NO: 6 followed by SEQ ID NO: 4 followed by amino acid residues 671–714 of SEQ ID NO: 2.

24. A method according to claim 5, wherein the modified Aβ or APP polypeptide, from the N- to the C-terminus, consists of amino acid residues 672–713 of SEQ ID NO: 2 followed by SEQ ID NO: 6 followed by amino acid residues 729–734 of SEQ ID NO: 2 followed by SEQ ID NO: 4 followed by amino acid residues 750–770 of SEQ ID NO: 2.

* * * * *